(12) United States Patent
Qiu

(10) Patent No.: US 11,103,660 B2
(45) Date of Patent: Aug. 31, 2021

(54) ATOMIZER AND ELECTRONIC CIGARETTE HAVING SAME

(71) Applicant: JOYETECH EUROPE HOLDING GMBH, Zug (CH)

(72) Inventor: Wei-Hua Qiu, ChangZhou (CN)

(73) Assignee: JOYETECH EUROPE HOLDING GMBH, Zug (CH)

( * ) Notice: Subject to any disclaimer, the term of this patent is extended or adjusted under 35 U.S.C. 154(b) by 530 days.

(21) Appl. No.: 16/016,665

(22) Filed: Jun. 25, 2018

(65) Prior Publication Data

US 2018/0303166 A1    Oct. 25, 2018

Related U.S. Application Data

(63) Continuation-in-part of application No. PCT/CN2017/081725, filed on Apr. 24, 2017.

(30) Foreign Application Priority Data

Jun. 8, 2016 (CN) .......................... 201620555514.8
Dec. 14, 2016 (CN) .......................... 201611156457.7

(51) Int. Cl.
| | |
|---|---|
| *A24F 47/00* | (2020.01) |
| *A61M 15/06* | (2006.01) |
| *A61M 11/04* | (2006.01) |
| *A24F 40/40* | (2020.01) |
| *A24F 40/485* | (2020.01) |

(Continued)

(52) U.S. Cl.
CPC ............. *A61M 15/06* (2013.01); *A24F 40/40* (2020.01); *A24F 40/485* (2020.01); *A24F 40/51* (2020.01); *A61M 11/042* (2014.02); *F16K 24/04* (2013.01); *A24F 40/10* (2020.01); *A61M 2205/0211* (2013.01); *A61M 2205/0272* (2013.01);

(Continued)

(58) Field of Classification Search
CPC ........ A24F 40/10; A24F 40/40; A24F 40/485; A24F 47/008
See application file for complete search history.

(56) References Cited

U.S. PATENT DOCUMENTS

2017/0196273 A1   7/2017   Qiu
2017/0280779 A1   10/2017  Qiu
2017/0325504 A1*  11/2017  Liu ...................... A61M 11/042

FOREIGN PATENT DOCUMENTS

| CN | 101084801 A | 12/2007 |
|---|---|---|
| CN | 103750569 A | 4/2014 |

(Continued)

*Primary Examiner* — Eric Yaary
(74) *Attorney, Agent, or Firm* — ScienBiziP, P.C.

(57) ABSTRACT

An atomizer comprises an outer tube, a liquid storing member received in the outer tube, and an atomizing head located at the lower portion of the liquid storing member. A liquid storing cavity is formed in the liquid storing member. An air outlet channel is formed between the outer tube inner wall and the liquid storing member outer wall. An atomizing cavity communicating with the liquid storing cavity and the air outlet channel is formed in the atomizing head. When the liquid tobacco absorbed by the atomizing head is insufficiently atomized, the liquid storing member above the atomizer head acts as a stopper, small smoke droplets can only be released from both sides of the atomizing head, preventing user inhalation of non-atomized liquid. An electronic cigarette having the atomizer is also provided.

9 Claims, 14 Drawing Sheets

(51) Int. Cl.
  *A24F 40/51* (2020.01)
  *F16K 24/04* (2006.01)
  *A24F 40/10* (2020.01)

(52) U.S. Cl.
  CPC ............... *A61M 2205/3334* (2013.01); *A61M 2205/8206* (2013.01)

(56) References Cited

FOREIGN PATENT DOCUMENTS

| | | |
|---|---|---|
| CN | 204540824 U | 8/2015 |
| CN | 105876869 A | 8/2016 |
| CN | 106136331 A | 11/2016 |

\* cited by examiner

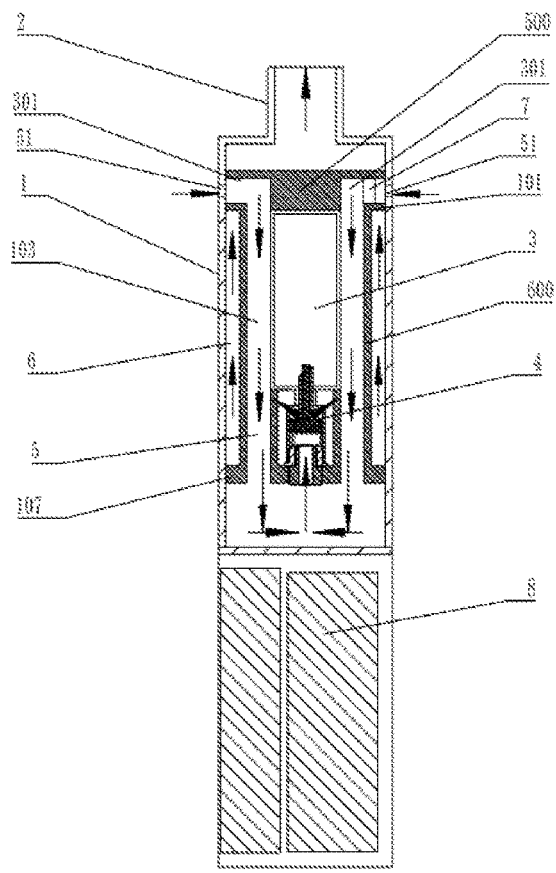
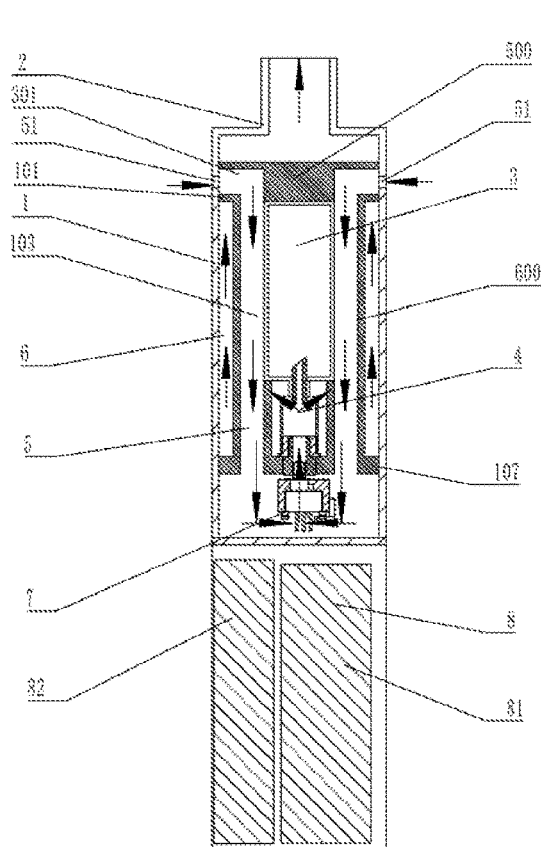
FIG.15    FIG.16
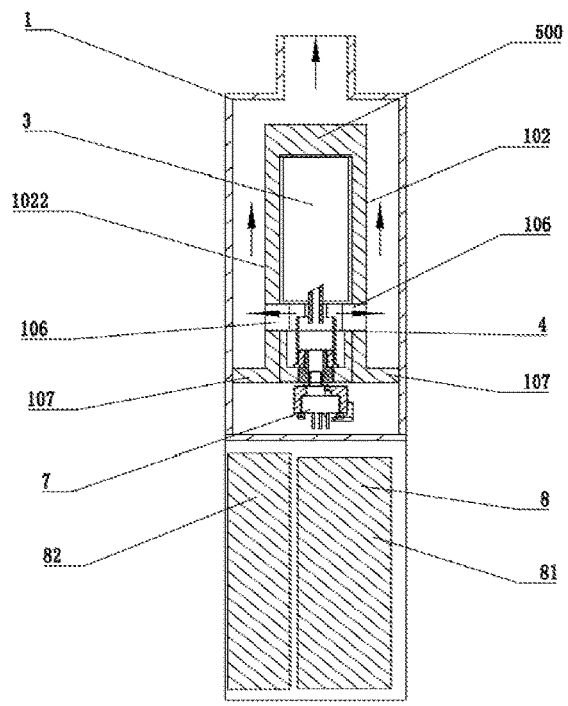
FIG.17

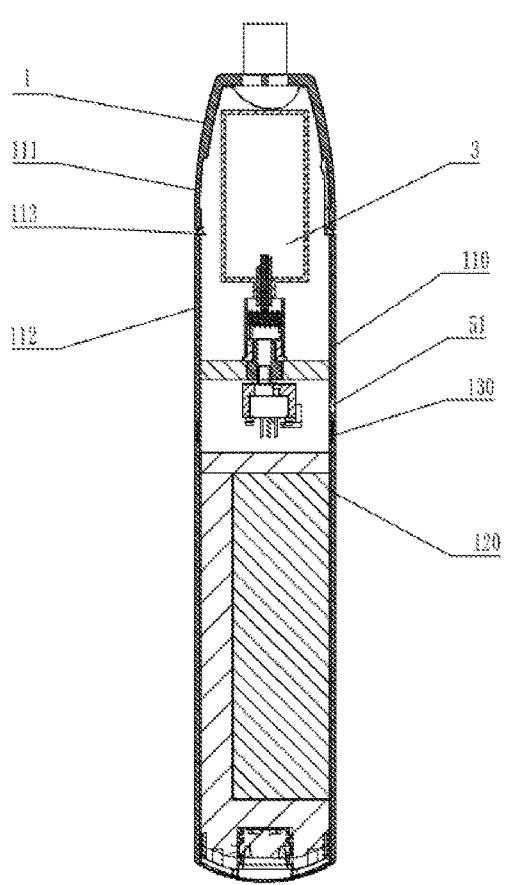
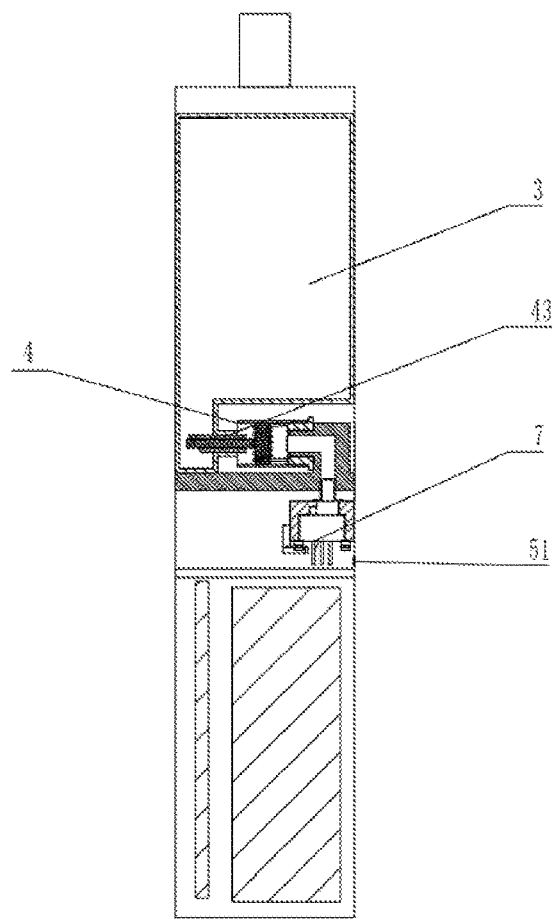
FIG.21    FIG.22
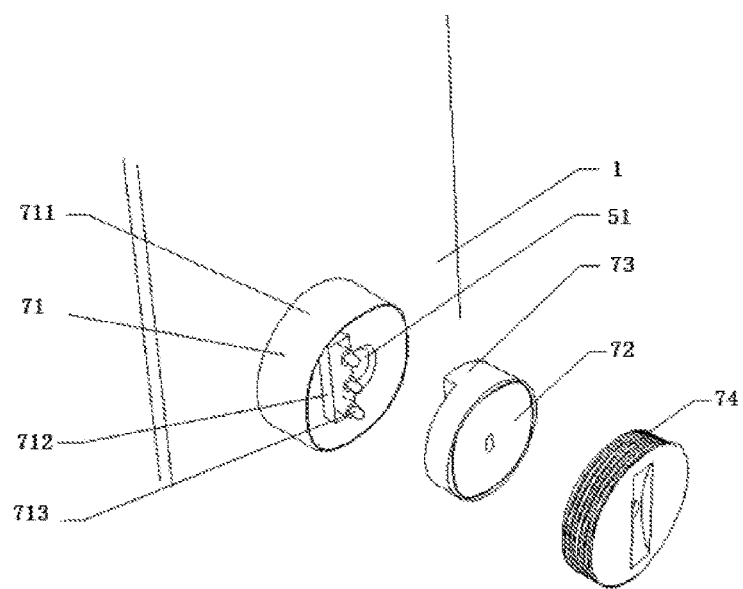
FIG.23

ATOMIZER AND ELECTRONIC CIGARETTE HAVING SAME

FIELD

The subject matter herein generally relates to electronic cigarettes, and particularly to an atomizer and an electronic cigarette having the atomizer.

BACKGROUND

Electronic cigarette mainly includes an atomizer. The core component of the atomizer is an atomizing head. The main function of the atomizing head is to heat and atomize the liquid tobacco. When heated, the liquid tobacco makes smoke. The smoke is mixed with air, and then enters the user's mouth. In a current atomizing head, the smoke flows out from the top portion of the atomizing head, and the smoke enters the user's mouth by an air outlet channel defined in the top portion of the atomizing head. When the liquid tobacco absorbed by the atomizing head is insufficiently atomized, the liquid tobacco can flow out from the air outlet channel of the atomizer head to enter directly into the user's mouth as a liquid. This situation is undesirable.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

FIG. 15 is a schematic view of an electronic cigarette, in accordance with a second exemplary embodiment of the fifth embodiment.

FIG. 16 is another schematic view of the electronic cigarette, in accordance with a second exemplary embodiment of the fifth embodiment.

FIG. 17 is a schematic view of the electronic cigarette of FIG. 16 rotated 90 degrees around the center axis.

FIG. 21 is a schematic view of an electronic cigarette, in accordance with a fourth exemplary embodiment of the fifth embodiment.

FIG. 22 is a schematic view of an electronic cigarette, in accordance with a third exemplary embodiment of the fifth embodiment.

FIG. 23 is a stereoscopic, exploded view of an air flow sensor, in accordance with a fifth exemplary embodiment of the fifth embodiment.

DETAILED DESCRIPTION

Figure 1:
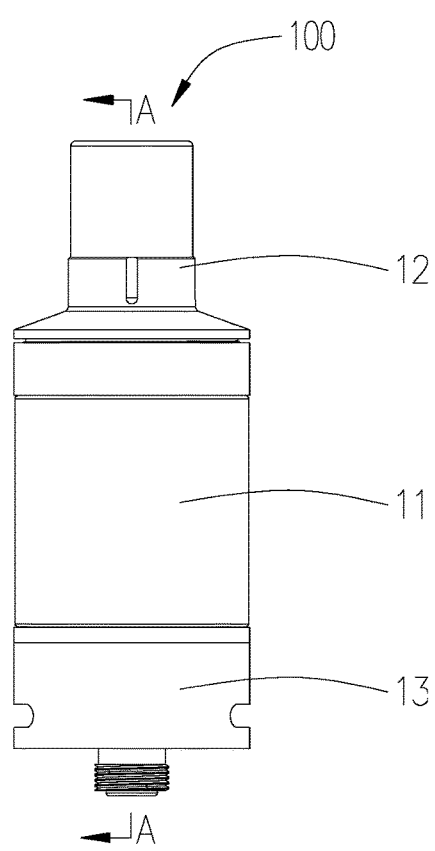
FIG. 1 is a schematic view of an atomizer, in accordance with a first embodiment of the present disclosure.

Specific embodiments of the present disclosure are described with reference to the accompanying drawings. A number of specific details are set forth in the following description, but the present disclosure can be implemented in many ways different from those described herein, and those skilled in the art can make improvements without violating the contents of the present disclosure. Therefore, the present disclosure is not to be considered as limiting the scope of the embodiments described herein.

Several definitions that apply throughout this disclosure will now be presented.

The term "coupled" is defined as coupled, whether directly or indirectly through intervening components, and is not necessarily limited to physical connections. The connection may be such that the objects are permanently coupled or releasably coupled. The term "substantially" is defined to be essentially conforming to the particular dimension, shape, or other feature that the term modifies, such that the component need not have that exact feature. The term "comprising," when utilized, means "including, but not necessarily limited to"; it specifically indicates open-ended inclusion or membership in the so-described combination, group, series, and the like.

When an element is considered to be "fixed to" another element, it can be either directly fixed on another element or indirectly fixed on another element with a centered element. When an element is considered to be "coupled with" another element, it can be either directly coupled with another element or indirectly coupled with another element with a centered element at the same time.

Unless otherwise defined, all technical and scientific terms used herein have the same meaning as commonly understood by one skilled in the art. The terms used in a specification of the present disclosure herein are only for describing specific embodiments, and are not intended to limit the present disclosure. The terms "and/or" used herein includes any and all combinations of one or more of associated listed items.

FIGS. 1-5 show a first embodiment of an electronic cigarette. The electronic cigarette includes an atomizer 100 and a battery assembly (not shown in figures). The atomizer 100 includes an outer tube 11, an upper cover assembly 12 detachably arranged on the top portion of the outer tube 11, a base assembly 13 detachably arranged on the bottom portion of the outer tube 11, a liquid storing assembly 14 received in the outer tube 11, and an atomizing head 15 detachably arranged on the base assembly 13.

Figure 2:
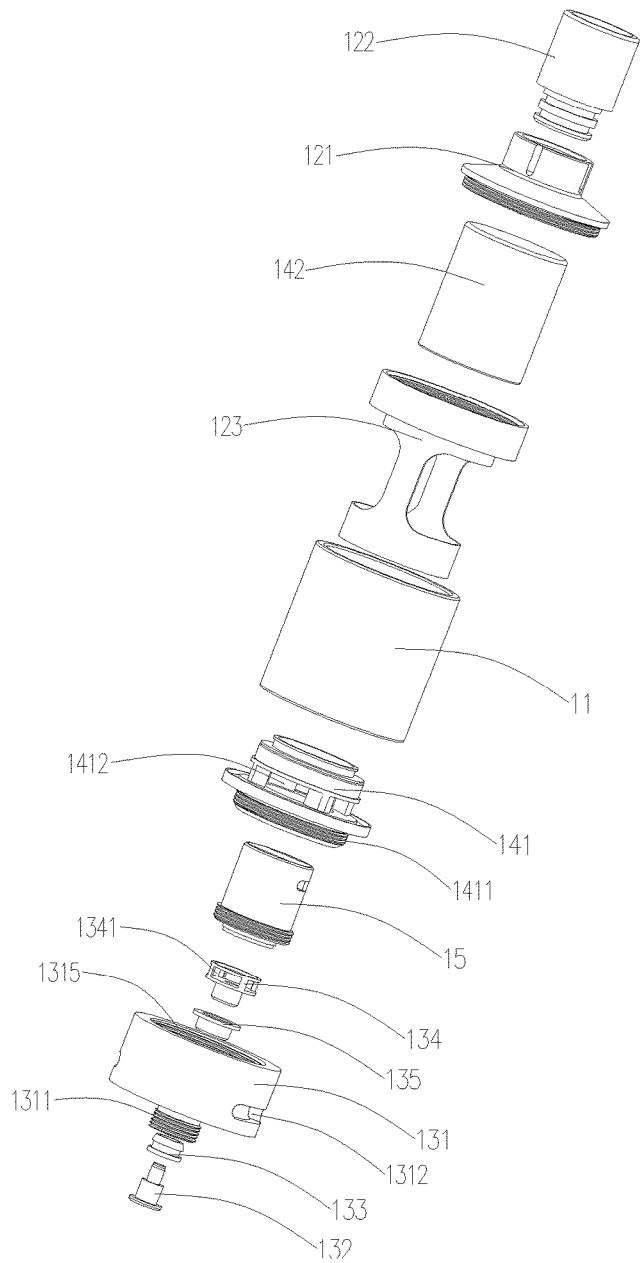
FIG. 2 is a stereoscopic, exploded view of the atomizer shown in FIG. 1.

Referring to FIG. 2, the outer tube 11 is substantially a hollow tubular structure with openings at both ends. The outer tube 11 is made of transparent or semi-transparent material, to allow observation of the amount of liquid tobacco remaining in the liquid storing assembly 14. In the illustrated embodiment, the outer tube 11 is made of glass.

The upper cover assembly 12 includes an upper cover 121 positioned on the top end of the outer tube 11, and a cigarette holder 122 detachably arranged on the upper cover 121.

The upper cover 121 is a substantially funnel. The cigarette holder 122 is a substantially hollow tube. The bottom end of the cigarette holder 122 is fitted in the cylindrical portion of the upper cover 121. The inside of the cigarette holder 122 is communicates with the inside of the upper cover 121.

Furthermore, an air outlet 1211 communicating with the inner cavity of the upper cover 121 is defined at the bottom of the upper cover 121.

In other embodiments, the cigarette holder 122 can be connected with the upper cover 121 by (for example) magnetic connection or threaded connection. Furthermore, the cigarette holder 122 and the upper cover 121 can be an integrated or unitary structure. The top end of the upper cover 121 has a longitudinal axis that is coaxial with a longitudinal axis of the cigarette holder 122.

The base assembly 13 includes a base 131, a first electrode 132 arranged on the base 131, a first insulating member 133 arranged on the base 131, a second electrode 134 arranged on the base 131, and a second insulating member 135 arranged on the base 131.

The base 131 is substantially annular. The base 131 has a longitudinal axis. A hollow connecting tube 1311 is communicated with the inner cavity of the base 131 and the longitudinal axis of the base 131 and the longitudinal axis of the connecting tube 1311 are coaxial. Typically, when in use, the connecting tube 1311 extends downwardly along the axial direction of the base 131. The connecting tube 1311 is connected with the battery assembly (not shown in FIGs) via threads defined on the outer circumference side of the connecting tube 1311. When in a smoking orientation, the first electrode 132 is at the bottom end of the connecting tube 1311 and the second electrode 134 is at the top end of the connecting tube 1311. The first electrode 132 is electrically connected with the battery assembly (not shown in FIGs). The top end of the first electrode 132 is electrically connected with a portion of the second electrode 134.

The first insulating member 133 is sandwiched between the first electrode 132 and the connecting tube 1311. The second insulating member 135 is sandwiched between the second electrode 134 and the connecting tube 1311.

Two first air inlets 1312 are defined on the sidewall of the base 131 and arranged opposite each other. A second air inlet 1341 is defined on the second electrode 134. The second air inlet 1341 communicates with the sidewall and top portion of the second electrode 134. The second air inlet 1341 communicates with the first air inlet 1312. The number of first air inlets can be one or more.

A flange 1313 is positioned at the middle portion of the inner wall of the base 131 along the axial direction. A first internal thread 1314 is defined on the inner wall of the flange 1313. A second internal thread 1315 is defined on the inner wall of the base 131.

The liquid storing assembly 14 includes a fixing member 141 and a liquid storing member 142 fixed to the fixing member 141.

The fixing member 141 is a substantially hollow tube with openings at both ends. A second external thread 1411 is defined on the bottom end of the fixing member 141, and the second external thread 1411 is matched with the second internal thread 1315. The fixing member 141 is connected with the base 131 by the threads. A third air outlet 1412 is defined on the sidewall of the fixing member 141, and the third air outlet 1412 communicates with the inner cavity of the fixing member 141.

The bottom end of the outer tube 11 abuts the fixing member 141.

The liquid storing member 142 is a substantially hollow tube. A liquid storing cavity 1421 is defined in the liquid storing member 142 to store the liquid tobacco. A liquid outlet 1422 communicating with the liquid storing cavity 1421 is defined at the bottom end of the liquid storing member 142. The liquid outlet 1422 communicates with the inner cavity of the fixing member 141. Furthermore, the liquid storing member 142 is made of a transparent material, such as glass, to allow a user to observe the remaining amount of the liquid tobacco. The bottom end of the liquid storing member 142 is tightly sleeved to the top end of the fixing member 141.

Furthermore, an air outlet channel 1423 is formed by the space between the external wall of the liquid storing member 142 and the internal wall of the outer tube 11. The air outlet channel 1423 communicates with the third air outlet 1412.

The atomizer 100 of the first embodiment further includes a connecting member 123 sleeved on the liquid storing member 142. The connecting member 123 is a substantially tube. The lower end of the connecting member 123 is fixed to the top portion of the fixing member 141 using an interference fit. The upper end of the connecting member 123 is connected with the upper cover 121 using threads. The connecting member 123 is made of transparent materials, to allow a user to observe the remaining amount of the liquid tobacco in the liquid storing member 142.

The upper end of the outer tube 11 abuts against the connecting member 123. A through hole 1231 is defined on the connecting member 123, and the through hole 1231 communicates with the air outlet channel 1423 and the air outlet 1211.

In other embodiments, the connecting member 123 can be omitted. In such embodiments, the lower end of the upper cover 121 is connected with the upper end of the outer tube 11 by threaded connection, clamped connection, or magnetic connection.

Figure 3:
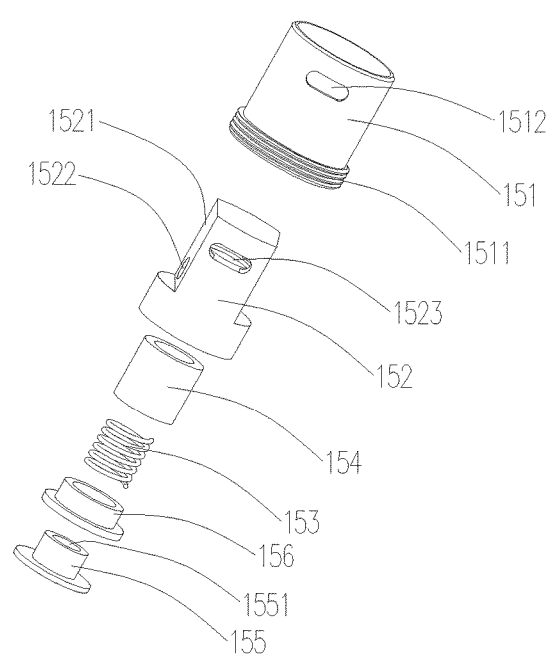
FIG. 3 is a stereoscopic, exploded view of the atomizing head shown in FIG. 2.

Referring to FIG. 3, the atomizing head 15 includes an atomizing tube 151, an atomizing head base 152 received in the atomizing tube 151, a heating element 153 arranged in the atomizing head base 152, a liquid guiding element 154 arranged in the atomizing head base 152, a third electrode 155 arranged at the lower end of the atomizing head base 152, and a third insulating member 156 arranged at the lower end of the atomizing head base 152.

The atomizing tube 151 is a substantially hollow tube with openings at both ends. A first external thread 1511, matching the first internal thread 1314, is defined on the external wall of the atomizing tube 151. The atomizing tube 151 is connected with the base 121 by the threads, and the external wall of the atomizing tube 151 is tightly attached to the inner wall of the fixing member 141.

Furthermore, a second air outlet 1512, communicating with the third air outlet 1412, is defined on the sidewall of the atomizing tube 151.

The atomizing head base 152 is a substantially hollow tube with openings at both ends. An atomizing cavity 1524 is formed in the atomizing head base 152. Two liquid inlet grooves 1521 are defined on the external wall of the atomizing head base 152. The liquid inlet grooves 1521 are positioned opposite each other on the external wall, and the liquid inlet grooves 1521 communicates with the liquid outlet 1422. Each liquid inlet groove 1521 includes a penetration hole 1522. The penetration hole 1522 is defined on the wall of the liquid inlet grove 1521, and the penetration hole 1522 communicates with the atomizing cavity 1524. In other embodiments, the quantity of liquid inlet grooves 1521 could be one or more.

A first air outlet 1523 is defined on the sidewall of the atomizing head base 152, and the first air outlet 1523 communicates with the second air outlet 1512 and the atomizing cavity 1524.

The heating element 153 and the liquid guiding element 154 are intertwined with each other, and received in the atomizing cavity 1524. The liquid guiding element 154 is attached to the penetration hole 1522. In the illustrated embodiment (FIG. 3), the liquid guiding element 154 is wrapped around the heating element 153. The heating element 153 may be a thermal fuse, and the liquid guiding element 154 may be made of cotton. In other embodiments, the liquid guiding element could be a combination of an element or a combination of ceramics, fiber rope, porous ceramics, foam metal, and foam graphite.

The upper end of the third electrode 155 is electrically connected with the heating element 153. The lower end of the third electrode 155 is electrically connected with the second electrode 134. A third air inlet 1551 is defined at the center of the third electrode 155, and the third air inlet 1551 communicates with the atomizing cavity 1524 and the second air inlet 1341. The third insulating member 156 is sandwiched between the third electrode 155 and the atomizing head base 152.

The processes of the atomizer 100 are as follows.

Figure 4:
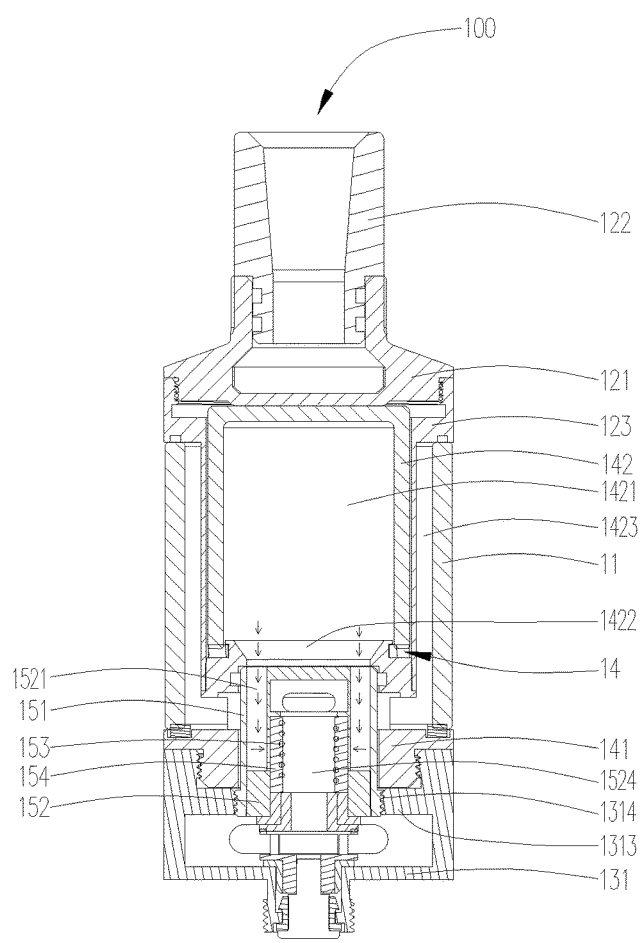
FIG. 4 is a cross-sectional view along line A-A of the atomizer shown in FIG. 1.
Figure 5:
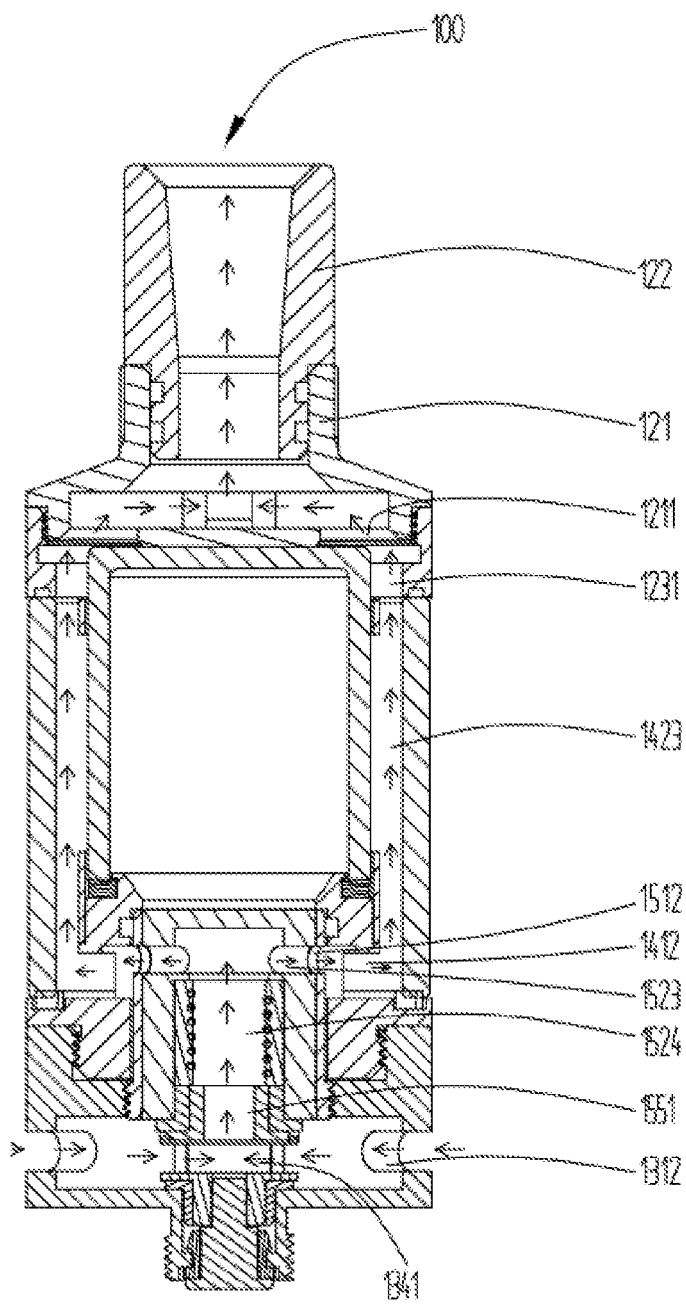
FIG. 5 is a cross-sectional view of the atomizer shown in FIG. 1.

Referring to FIG. 4, the liquid tobacco in the liquid storing cavity 1421 flows out the liquid outlet 1422, through the liquid inlet groove 1521 and the penetration hole 1522 in turn, and enters the atomizing cavity 1524. Then, the liquid tobacco is absorbed by the liquid guiding element 154, and heated by the heating element 153 to generate smoke. The atomizing cavity 1524 fills with smoke. The direction of the arrows in FIG. 4 is the flow direction of the liquid tobacco. Referring to FIG. 5, when the user inhales, external air enters the first air inlet 1312, passes through the second air inlet 1341 and the third air inlet 1551, and enters the atomizing cavity 1524 and mixes with the smoke. The air/smoke mixture passes through the first air outlet 1523, the second air outlet 1523, the third air outlet 1412, the air outlet channel 1423, the through hole 1231, the air outlet 1211, the upper cover 121, and the cigarette holder 122 in turn, to enter the user's mouth. The direction of the arrow in FIG. 5 is the flow direction of the air flow during an inhale.

Furthermore, the liquid storing member 142 can be removed by separating the upper cover 121. The base 131 can be separated for changing the atomizing head 15.

In the first embodiment, the liquid enters the atomizer 100 from the upper portion of the atomizing head 15, and the air/smoke mixture comes from the sides of the atomizing head 15. When the liquid tobacco absorbed by the atomizing head 15 is insufficiently atomized, the liquid storing member 142 above the atomizer head 15 can act as a stopper. The small droplets of liquid tobacco can only be released from both sides of the atomizing head 15, thus avoiding liquid tobacco droplets from the position above the atomizer head 15 and enter into the user's mouth.

Figure 6:
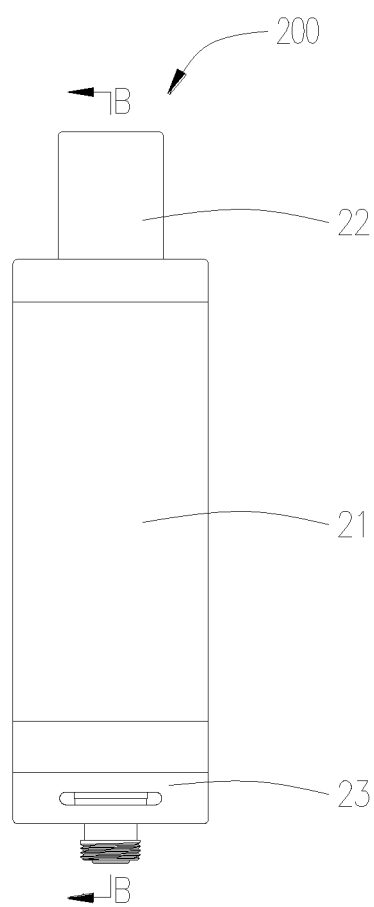
FIG. 6 is a schematic view of an atomizer, in accordance with a second embodiment of the present disclosure.
Figure 7:
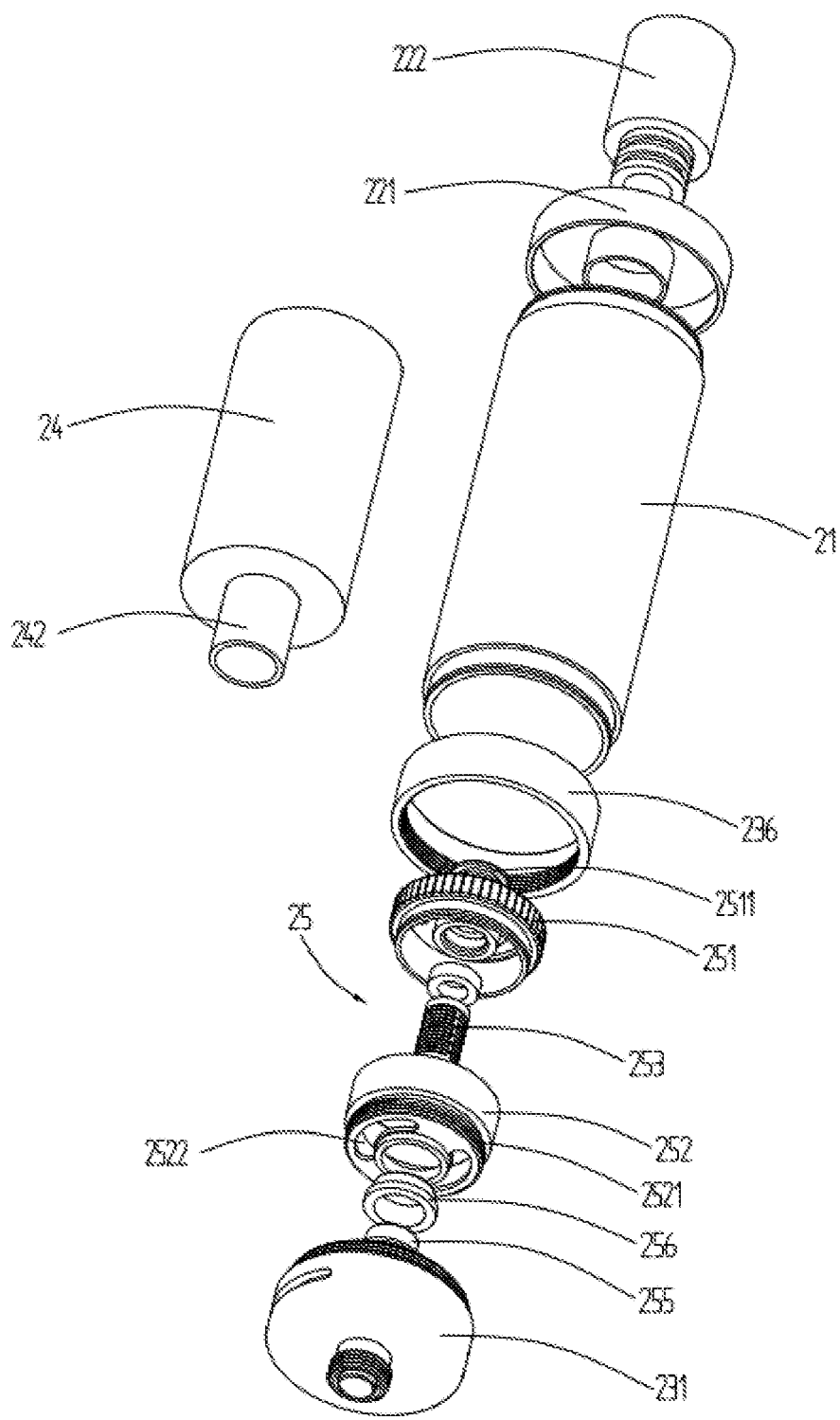
FIG. 7 is a stereoscopic, exploded view of the atomizer shown in FIG. 6.
Figure 8:
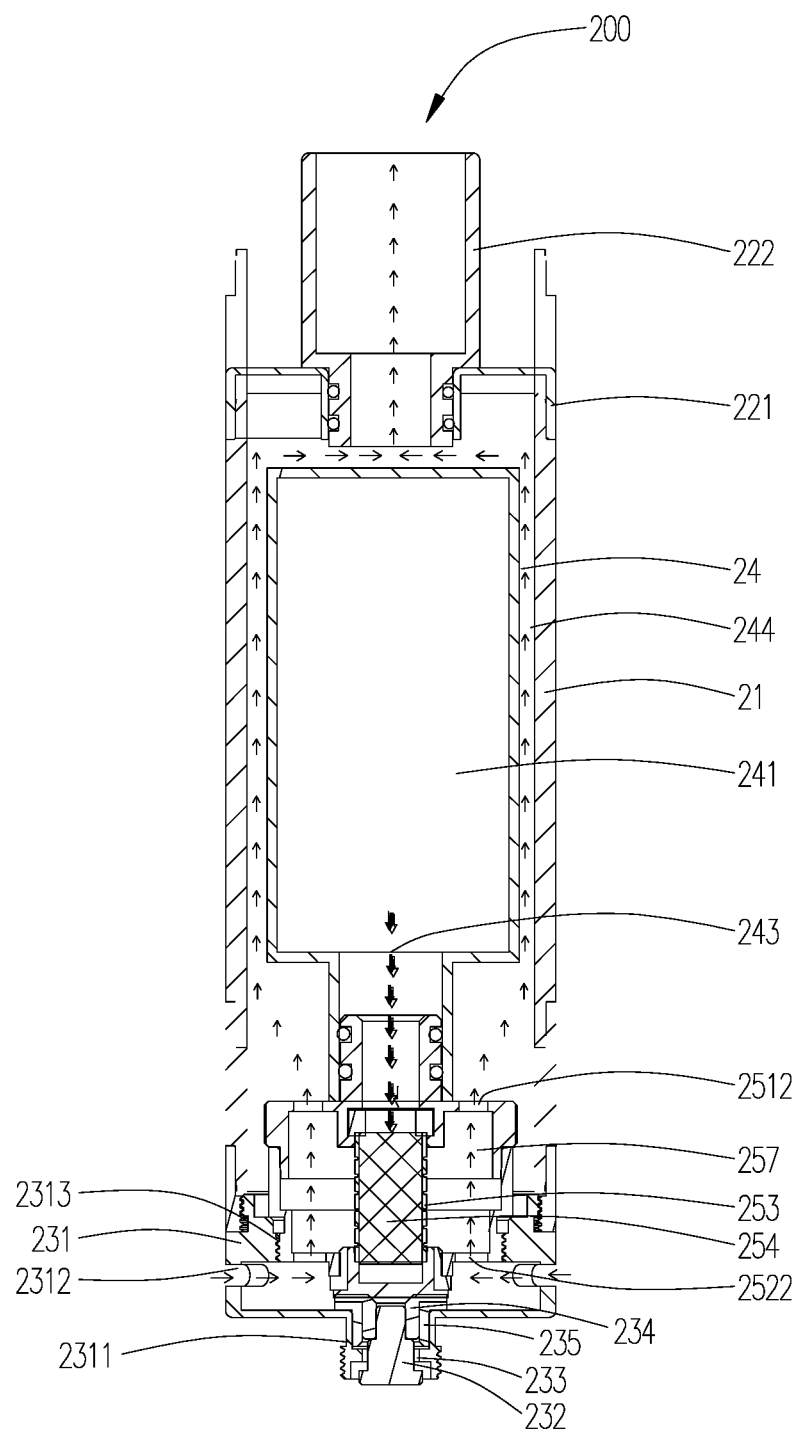
FIG. 8 is a cross-sectional view along line B-B of the atomizer shown in FIG. 6.

FIGS. 6-8 show a second embodiment of an electronic cigarette. The electronic cigarette includes an atomizer 200 and a battery assembly (not shown in FIGs) connected with the atomizer 200. The atomizer 200 includes an outer tube 21, an upper cover assembly 22, a base assembly 23, a liquid storing assembly 24, and an atomizing head 25. The upper cover assembly 22 is detachably arranged on the upper end of the outer tube 21. The base assembly 23 is detachably arranged at the lower end of the outer tube 21. The liquid storing assembly 24 is received in the outer tube 21. The atomizing head 25 is detachably arranged on the base assembly 23.

The outer tube 21 is a substantially hollow tube with openings at both ends. The outer tube 21 is made of transparent or semi-transparent materials to allow observation of the amount of liquid tobacco remaining in the liquid storing assembly 24. In the second embodiment, the outer tube 21 is made of glass.

The upper cover assembly 22 includes an upper cover 221 detachably arranged on the upper end of the outer tube 21 and a cigarette holder 222 detachably arranged on the upper cover 211. The upper cover 221 is a substantially disk-like structure. The cigarette holder 222 is a substantially tube. The cigarette holder 222 is connected to the center of the upper cover 221, and communicates with the upper cover 221.

In the illustrated embodiment (FIG. 7), the upper cover 221 is connected with the outer tube 21 using an interference fit. The cigarette holder is fitted in the upper cover 221. In other embodiments, the upper cover 221 can be connected with the outer tube 21 by threaded connection, clamped connection, or magnetic connection. The upper cover 221 also can be connected with the cigarette holder 222 by threaded connection, clamped connection, or magnetic connection.

The base assembly 23 include a base 231, a first electrode 232 arranged at the lower end of the base 231, a first insulating member 233, a second electrode 234, a second insulating member 235, and a connecting member 236 arranged on the upper end of the base 231.

The base 231 is substantially annular. The base 231 has a longitudinal axis. A connecting tube 2311 is communicated with the inner cavity of the base 231, and the longitudinal axis of the base 231 and the longitudinal axis of the connecting tube are coaxial. Typically, when in use, the connecting tube 2311 is extends downwardly along the longitudinal axis of the base 231. The connecting tube 2311 is connected with the battery assembly (not shown in FIGs) by threads defined on the outer circumference side of the connecting tube 2311. The first electrode 232 is positioned at the lower end of the connecting tube 2311. The second electrode 234 is positioned at the upper end of the connecting tube 2311. The lower end of the first electrode 232 is electorally connected with the battery assembly (not shown in FIGs). The upper end of the first electrode 232 is electorally connected with a portion of the second electrode 234.

The first insulating member 233 is sandwiched between the first electrode 232 and the connecting tube 2311. The second insulating member 235 is sandwiched between the second electrode 234 and the connecting tube 2311.

Two first air inlets 2312 are defined on the sidewall of the base 231 and arranged opposite each other. The first air inlets 2312 communicated with the inner cavity of the base 231. Internal threads 2313 are defined on the internal wall of the base 231.

The connecting member 236 is substantially annular. The lower end of the connecting member 236 is connected with the upper end of the base 231 by threads. The upper end of the connecting member 236 is connected with the lower end of the outer tube 21 using an interference fit. Therefore, the outer tube 21 is connected with the base 231 via the connecting member 236. In other embodiments, the connecting member 236 can be left out, and the outer tube 21 can be connected with the base 231 directly by threaded connection, clamped connection, or magnetic connection.

The liquid storing assembly 24 is a substantially hollow tube with an opening at the lower end. A liquid storing cavity 241 is formed by the inner space of the liquid storing assembly 24. A liquid outlet 243 is defined at the bottom center of the liquid storing assembly 24, and communicates with the liquid storing cavity 241. The bottom center of the liquid storing assembly 24 extends along the axial direction of the liquid storing assembly 24 to form a connecting portion 242. The connecting portion 242 communicates with the liquid storing cavity 241.

Furthermore, an air outlet channel 244 is formed by the space between the external wall of the liquid storing assembly 24 and the internal wall of the outer tube 21. The air outlet channel 244 communicates with the cigarette holder 222.

The atomizing head 25 includes an atomizing upper cover 251 connected with the liquid storing assembly 24, an atomizing lower cover 252 connected with the base 231, a heating element 253 positioned between the atomizing upper cover 251 and the atomizing lower cover 252, a liquid guiding element 254 positioned between the atomizing upper cover 251 and the atomizing lower cover 252, a third electrode 255 arranged on the atomizing lower cover 252, and a third insulating member 256 arranged on the atomizing lower cover 252.

The atomizing upper cover 251 is a substantially disk-like structure. The top center of the atomizing upper cover 251 extends along the axial direction of the atomizing upper cover 251 to form an installation portion 2511, and the installation portion 2511 communicates with the inner cavity of the atomizing upper cover 251. The installation portion 2511 is fitted in the connecting portion 242 of the liquid storing assembly 24 to connect the atomizing upper cover 251 and the liquid storing assembly 24 together. In other embodiments, the atomizing upper cover 251 can be connected with the liquid storing assembly 24 by threaded, clamped, or magnetic connection.

The atomizing lower cover 252 is a substantially disk-like structure. External threads 2521 are defined on the external wall of the atomizing lower cover 252, matching with the internal threads 2313. The atomizing lower cover 252 is connected with the base 231 by the threads. The upper end of the atomizing lower cover 252 is fixed to the lower end of the atomizing upper cover 251 using an interference fit. An atomizing cavity 257 is formed by the space between the atomizing upper cover 252 and the atomizing lower cover 251.

Two opposite air outlets 2512 are defined on the atomizing upper cover 251 and arranged opposite each other. The air outlets 2512 communicate with the air outlet channel 244 and the atomizing cavity 257. The second air inlets 2522 are defined on the atomizing lower cover 252. The second air inlets 2522 are communicated with the first air inlet 2312 and the atomizing cavity 257. In other embodiments, the quantity of air outlets 2512 and second air inlets 2522 can be three or more.

The third electrode 255 is arranged at the center of the lower end of the atomizing lower cover 252. The lower end of the third electrode 252 is electrically connected with the second electrode 234. The third insulating member 256 is sandwiched between the third electrode 255 and the atomizing lower cover 252.

The heating element 253 is tightly attached to the liquid guiding element 254, and positioned at the outside of the liquid guiding element 254. Specifically, the upper end of the liquid guiding element 254 is tightly attached to the lower end of the installation portion 2511 to absorb the liquid tobacco. The heating element 253 is electrically connected to the upper end of the third electrode 255.

The processes of the atomizer 200 in the second embodiment are as follows.

Referring to FIG. 4, the liquid tobacco in the liquid storing cavity 241 flows through the liquid outlet 243 and enters the atomizing cavity 257, then the liquid tobacco is absorbed by the liquid guiding element 254, and heated by the heating element 253 to generate smoke. Therefore, the atomizing cavity 257 fills with smoke. Referring FIG. 8, the direction of the thicker arrow is the flow direction of the liquid tobacco. When the user inhales, the external air passes through the first air inlet 2312 and the second air inlet 2522 and enters the atomizing cavity 257. The external air mixes with the smoke in the atomizing cavity 257. The air/smoke mixture passes through the air outlet 2512 and the air outlet channel 244, then flows into the user's mouth. Referring to FIG. 8, the direction of the thinner arrows is the direction of the air flow during an inhale.

In the second embodiment, the liquid enters the atomizer 200 from the upper portion of the atomizing head 25, and the air/smoke mixture comes out from the sides of the atomizing head 25. When the liquid tobacco absorbed by the atomizing head 25 is insufficiently atomized, the liquid storing assembly 24 above the atomizer head 25 acts as a stopper. The small droplets of liquid tobacco can only be released from both sides of the atomizing head 25, thus avoiding liquid tobacco droplets from flowing out from the position above the atomizer head 25 and enter into the user's mouth.

Figures 9, 10:
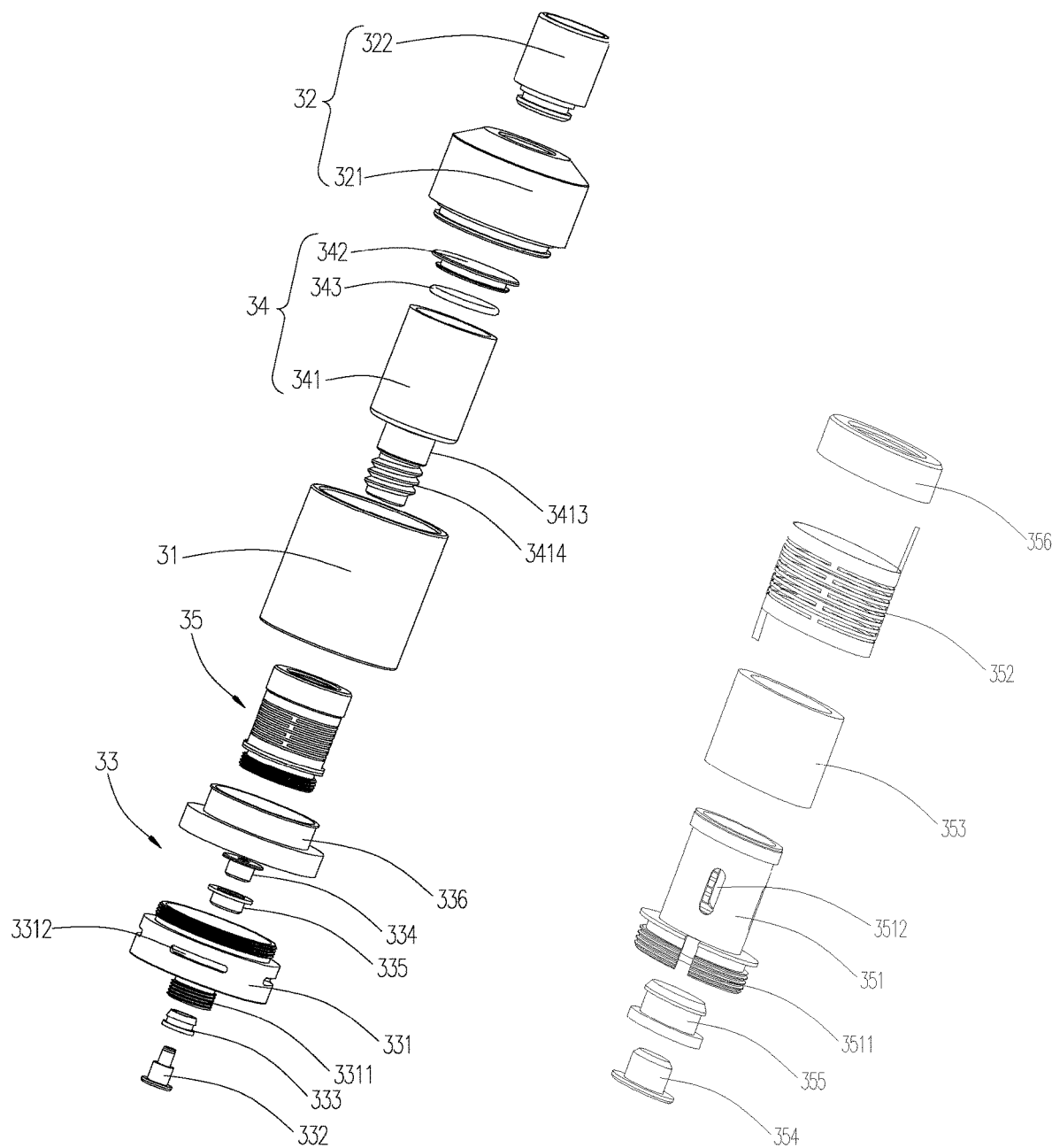
FIG. 9 is a stereoscopic, exploded view of an atomizer, in accordance with a third embodiment of the present disclosure.
FIG. 10 is a stereoscopic, exploded view of the atomizing head shown in FIG. 9.
Figures 11, 12:
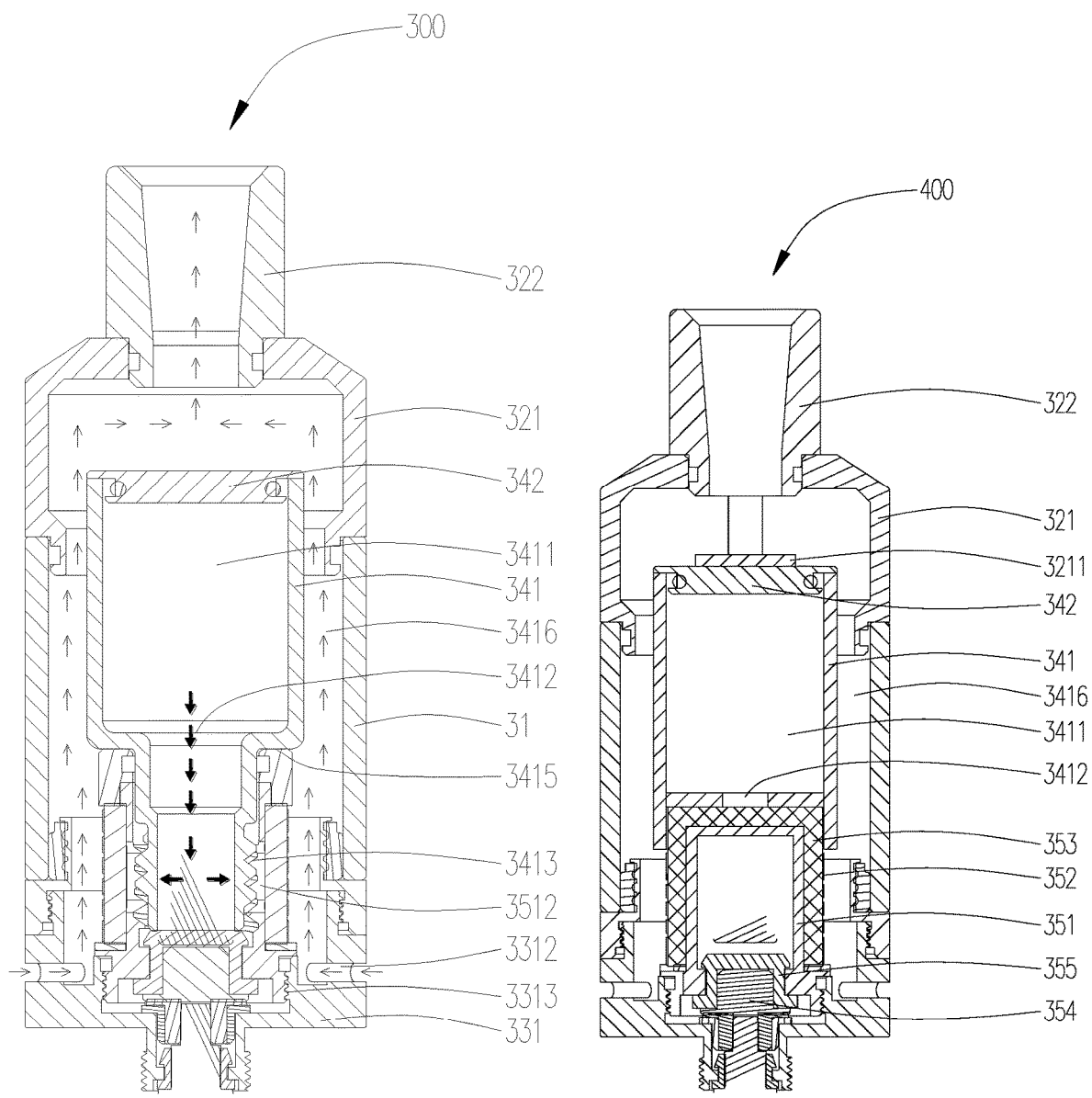
FIG. 11 is a cross-sectional view of the atomizer shown in FIG. 9.
FIG. 12 is a cross-sectional view of an atomizer, in accordance with a fourth embodiment of the present disclosure.

FIGS. 9-11 show a third embodiment of an electronic cigarette. The electronic cigarette includes an atomizer 300 and a battery assembly (not shown in FIGs) connected with the atomizer 300. The atomizer 300 includes an outer tube 31, an upper cover assembly 32 detachably arranged on the upper end of the outer tube 31, a base assembly 33 detachably arranged at the lower end of the outer tube 31, a liquid storing assembly 34 received in the outer tube 31, and an atomizing head 35 detachably arranged on the base assembly 33.

The outer tube 31 is a substantially tube with openings at both ends. The outer tube 31 is made of transparent or semi-transparent materials to allow observation of the amount of liquid tobacco remaining in the liquid storing assembly 34. In the third embodiment, the outer tube 31 is made of glass.

The upper cover assembly 32 includes an upper cover 321 detachably arranged on the upper end of the outer tube 31 and a cigarette holder 322 detachably arranged on the upper cover 322. The upper cover 321 and the cigarette holder 322 are substantially tubes. The cigarette holder 322 is connected to the center of the upper end of the upper cover 321, and communicates with the upper cover 321.

In the illustrated embodiment (FIG. 11), the lower end of the upper cover 321 is fitted in the upper end of the outer tube 31. The cigarette holder 322 is fitted in the center of the upper end of the upper cover 322. In other embodiments, the upper cover 321 can be connected with the outer tube 31 by threaded connection, clamped connection, or magnetic connection. The upper cover 321 also can be connected with the cigarette holder 322 by the same connections.

The base assembly 33 includes a base 331, a first electrode 332, a first insulating member 333, a second electrode 334, a second insulating member 335, and a connecting member 336 arranged on the upper end of base 331. The first electrode 332, the first insulating member 333, the second electrode 334, and the second insulating member 335 are arranged on the lower end of the base 331.

The base 331 is substantially annual. The base 331 has a longitudinal axis. A hollow connecting tube 3311 communicates with the inner cavity of the base 331, and the longitudinal axis of the base 331 and the longitudinal axis of the connecting tube 3311 are coaxial. Typically, when in use, the connecting tube 3311 extends downwardly along the axial direction of the base 331. The connecting tube 3311 is connected with the battery assembly (not shown in FIGs) by the threads. The first electrode 332 is arranged at the lower end of the connecting tube 3311. The second electrode 334 is arranged at the upper end of the connecting tube 3311. The lower end of the first electrode 332 is electrically connected with the battery assembly (not shown in FIGs). The upper end of the first electrode 332 is electrically connected with the second electrode 334.

Furthermore, the first insulating member 333 is sandwiched between the first electrode 332 and the connecting tube 3311. The second insulating member 335 is sandwiched between the second electrode 334 and the connecting tube 3311.

Furthermore, four first air inlets 3312 are equidistantly defined on the sidewall of the base 331. The first air inlets communicate with the inner cavity of the base 331. Internal threads 3313 are defined on the internal wall of the base 331.

In other embodiments, the number of first air inlets 3312 can be one or more.

The connecting member 336 is substantially annual. The lower end of the connecting member 336 is connected to the upper end of the base 331 by the threads. The upper end of the connecting member 336 connects with the lower end of the outer tube 31 using an interference fit. Therefore, the outer tube 31 is connected with the base 331 by the connecting member 336. In other embodiments, the connecting member 336 can be omitted. The outer tube 31 can connect with the base 331 by threaded, clamped, or magnetic connection.

The liquid storing assembly 34 includes a liquid storing member 341 and a liquid storing member head cover 342 arranged on the upper end of the liquid storing member 341.

The liquid storing member 341 is a substantially tube with an opening at the upper end. A liquid storing cavity 3411 is formed in the liquid storing member 341 to store the liquid tobacco. An air outlet channel 3416 is formed by the space between the external wall of the liquid storing member 341 and the internal wall of the outer tube 31. The air outlet channel 3416 communicates with the cigarette holder 322. A liquid outlet 3412 communicating with the liquid storing cavity 3411 is defined at the bottom center of the liquid storing member 341. The bottom center of the liquid storing member 341 extends along the axial direction to form a connecting portion 3413 communicating with the liquid storing cavity 3411. A first external thread 3414 is defined on the connecting portion 3413. A liquid outlet (not shown in FIGs) is defined on the sidewall of the connecting portion 3413 to communicate with the inner cavity of the connecting portion 3413.

Furthermore, the joint between the liquid storing member 341 and the connection portion 3413 forms a step surface 3415.

A sealing ring 343 is positioned at the joint between the liquid storing member head cover 341 and the liquid storing member 341 to promote sealing.

Referring to FIG. 10, the atomizing head 35 includes an atomizing head base 351, a heating element 352 sleeved to the atomizing head base 351, a liquid guiding element 353 sleeved to the atomizing head base 351, a third electrode 354 arranged at the lower end of the atomizing head base 351, a third insulating member 355 arranged at the lower end of the atomizing head base 351, and an atomizing head cover 356 positioned between the step surface 3415 and the upper end of the atomizing head base 351.

The atomizing head base 351 is a substantially tube with openings at both ends. External threads 3511 are defined at the lower end of the atomizing head base 351 to match with the internal threads 3313. First internal threads 3513 are defined on the internal wall of the atomizing head base 351 to match with the first external threads 3414. The atomizing head base 351 is connected to the base 331 by the threads. The liquid storing member 341 is connected with the atomizing head base 351 by the threads. In other embodiments, the atomizing head base 351 can be connected with the liquid storing member 341 by clamped connection or magnetic connection.

Furthermore, a penetration hole 3512 is defined on the sidewall of the atomizing head base 351.

The heating element 352 is a substantially heating tube. An atomizing cavity (not shown in figures) is formed in the heating element 352. A smoke outlet (not shown in figures) is defined on the heating element 352. The smoke outlet (not shown in figures) communicates with the atomizing cavity, the first air inlet 3312, and the air outlet channel 3416. The liquid guiding element 353 is positioned between the heating element 352 and the atomizing head base 351. The liquid guiding element 353 is attached to the heating element 352 and the atomizing head base 351. In the illustrated embodiment (FIG. 10), the liquid guiding element 353 is made of cotton. In other embodiments, the liquid guiding element 353 could be an element or a combination from ceramics, fiber rope, porous ceramics, foam metal, or foam graphite.

The third insulating member 355 is sealed at the lower end of the atomizing head base 351. The third electrode 354 is fixed to the third insulating member 355. Thereby, the third electrode 354 is insulated from the atomizing head base 351. Furthermore, the third electrode 354 is electrically connected with the heating element 352.

In other embodiments, the atomizing head cover 356 can be omitted. The upper end of the atomizing head base 351 abuts the step surface 3415 to limit the installation position of the liquid storing member 341.

The processes of the atomizer 300 in the third embodiment are as follows.

The liquid tobacco in the liquid storing cavity 3411 enters the connecting portion 3413 by the liquid outlet 3412. Then, the liquid tobacco passes through the penetration hole 3512, and the liquid tobacco is absorbed by the liquid guiding element 353. The heating element 353 heats the liquid tobacco to generate smoke. Therefore, the atomizing cavity fills with the smoke, and the smoke diffuses to outside of the heating element 352 via the smoke outlet (not shown in figures). Referring to FIG. 11, the direction of the thicker arrows is the flow direction of the liquid tobacco. When the user inhales, the external air passes through the first air inlet 3312, then mixes with the smoke. The air/smoke mixture passes through the air outlet channel 3416 and the cigarette holder 322, then enters the user's mouth. Referring to FIG. 11, the direction of the thinner arrows is the flow direction of the air flow.

The upper cover 321 and the liquid storing member head cover 342 can be separated for refilling or changing the liquid storing member 341.

In the third embodiment, the liquid enters the upper portion of the atomizing head 35, while the smoke with outside air comes out from the sides of the atomizing head 35. When the liquid tobacco is insufficiently atomized, the liquid storing member above the atomizer head acts as a stopper. The small droplets of liquid tobacco can only be released from both sides of the atomizing head, thus avoiding liquid tobacco droplets from flowing out from the position above the atomizer head and entering into the user's mouth.

FIG. 12 shows a fourth embodiment of an atomizer 400. The structure of the atomizer 400 is mostly same as the atomizer 300. The main difference is in the structure of the atomizing head base 351 in the atomizing head 35.

In the fourth embodiment, the atomizing head base 351 only has an opening defined at the lower end, used to install the third electrode 354 and the third insulating member 355. The upper end and the whole body of the atomizer head base 351 are sealing structures.

The liquid guiding element 353 is attached to the external wall of the atomizing head base 351 and the upper end of the atomizing head base 351. The lower end of the connection portion 3413 abuts the liquid guiding element 353. The liquid tobacco in the liquid storing cavity 3411 passes through the connecting portion 3413, and is absorbed by the liquid guiding element 353. In a specific embodiment of the fourth embodiment, the connecting portion 3413 is omitted. The bottom portion of the liquid storing member 341 abuts the liquid guiding element 353. The liquid tobacco passes through the liquid outlet 3413, and is absorbed by the liquid guiding element 353.

In order to support the liquid storing member 341, the upper end surface of the upper cover 321 extends along the axial direction to form a pressing member 3211. The pressing member 3211 communicates with the cigarette holder 322 and the air outlet channel 3416. When the upper cover 321 is arranged on the outer tube 31, the lower end of the pressing member 3211 can abut the liquid storing member head cover 342 arranged on the upper end of the liquid storing member 341. At the same time, the lower end of the liquid storing member 341 abuts the heating element 352. Therefore, both ends of the liquid storing member 341 are fixed, and thus the liquid storing member 341 is fixed.

The processes of the atomizer 400 are as in the third embodiment.

Comparing the atomizer 400 of the fourth embodiment with the atomizer 300 of the third embodiment, the structure of the atomizing head 35 is simplified. The simplified atomizing head 35 has the same function, and is easier to produce and use.

The fourth embodiment provides an electronic cigarette. The electronic cigarette includes the atomizer 400 and a battery assembly (not shown in figures) connected with the atomizer 400. The electronic cigarette has all the technical features of the atomizer 400, so that the technical effects of the electronic cigarette are the same as those of the atomizer 300.

A fifth embodiment is as follows.

A first specific embodiment of the fifth embodiment is as follows.

Figure 13:
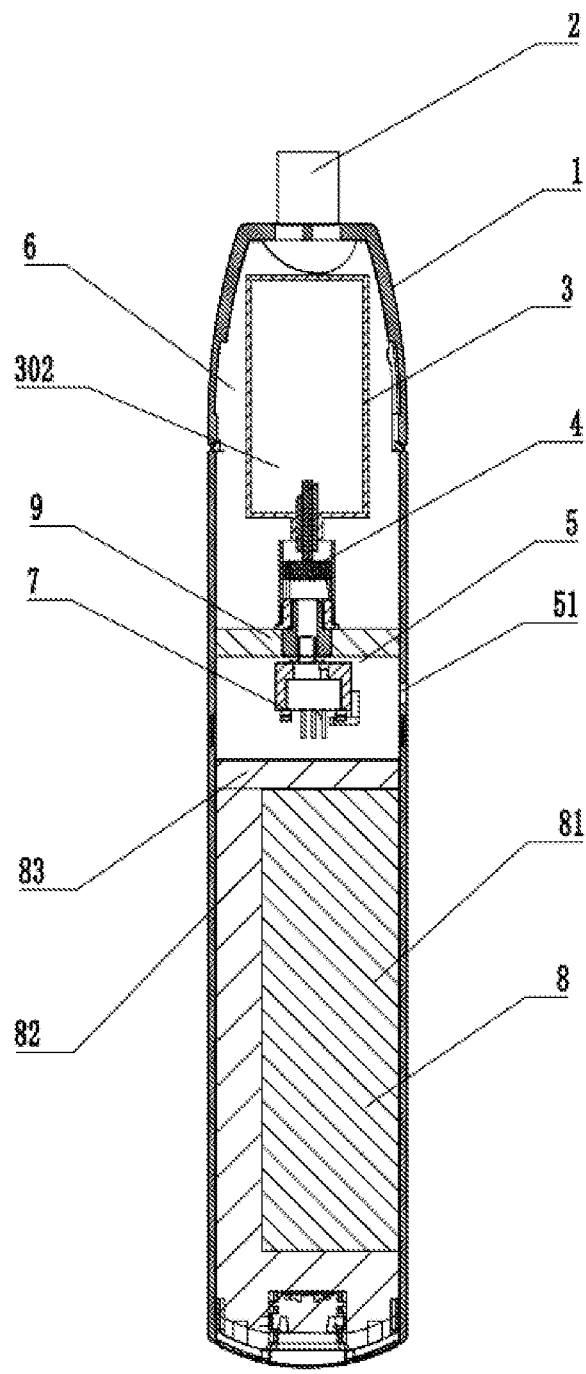
FIG. 13 is a schematic view of an electronic cigarette, in accordance with a first exemplary embodiment of a fifth embodiment.
Figure 14:
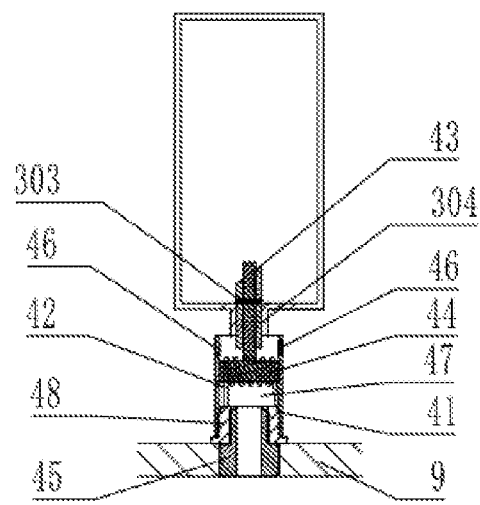
FIG. 14 is a schematic view of an atomizer of the electronic cigarette shown in FIG. 13.
Figure 18:
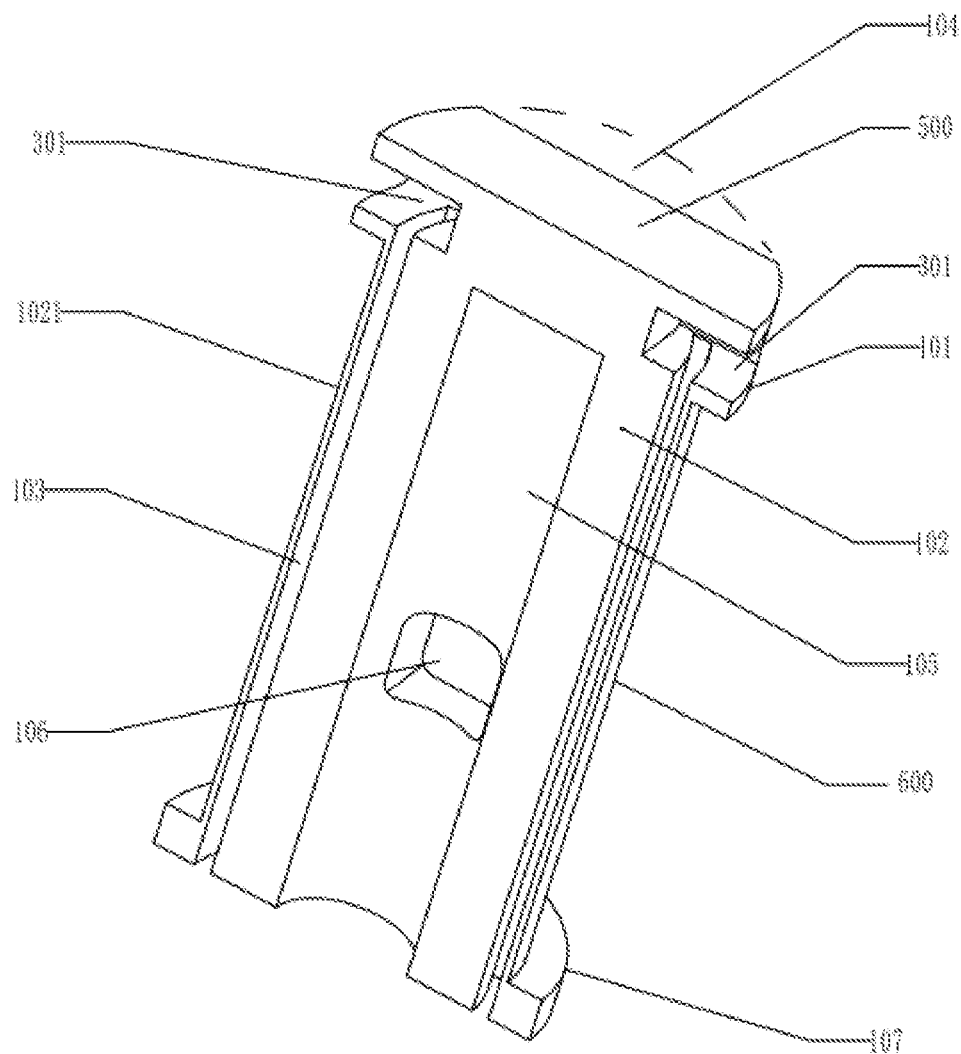
FIG. 18 is a cross-sectional view of a blocking portion and a first shell portion of the second exemplary embodiment of the fifth embodiment.
Figure 19:
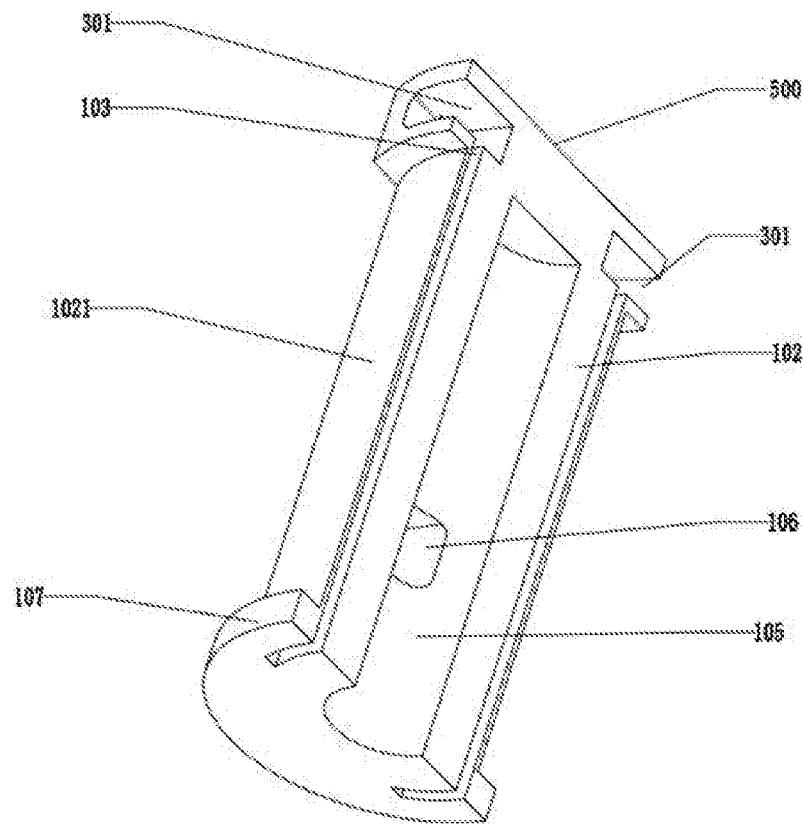
FIG. 19 is another cross-sectional view of the blocking portion and a first shell portion shown in FIG. 18.
Figure 20:
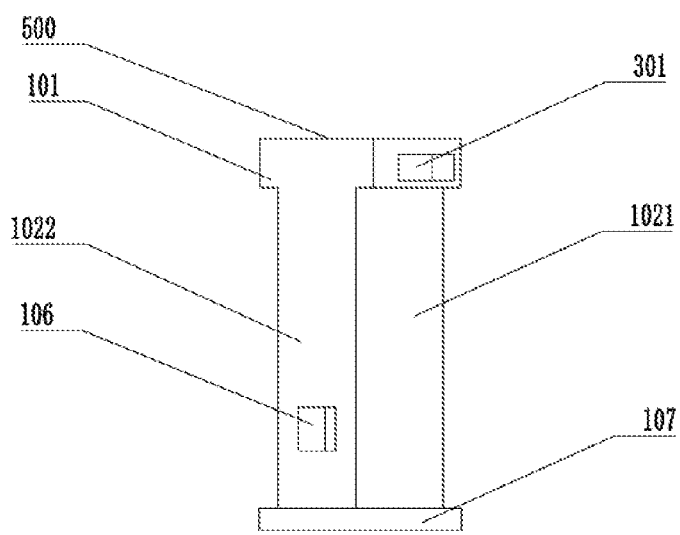
FIG. 20 is schematic view of the blocking portion and a first shell portion shown in FIG. 18.

Referring to FIGS. 13 and 14, the present disclosure provides an electronic cigarette. The electronic cigarette includes a housing 1 and a cigarette holder 2. The housing 1 is equipped with a liquid storing member 3, an atomizing head 4, an air inlet channel 5, an air outlet channel 6, a sensor 7, and a power supply and control assembly 8. The cigarette holder 2 is connected to the housing 1, and communicates with the air outlet channel 6. The liquid storing member 3 includes a liquid storing cavity 302. The atomizing head 4 is positioned outside of the liquid storing member 3, and is in communication with the liquid storing cavity 302. The air inlet channel 5 and the air outlet channel 6 are positioned outside of the liquid storing member 3. The air inlet channel 5 and the air outlet channel 6 communicate with the atomizing head 4. The sensor 7 and the atomizing head 4 are electrically connected with the power supply and control assembly 8. An air inlet 51 is positioned on the housing 1, and communicates with the air inlet channel 5. The sensor 7 is positioned in the air inlet channel 5. In the illustrated embodiment (FIG. 13), the sensor 7 is positioned inside of the air inlet channel 5, and adjacent to the air inlet 5. When the user inhales from the cigarette holder 2, a negative pressure is formed in the air inlet channel 5, so that the sensor 7 forms an electrical signal. The electrical signal is transmitted to the power supply and control assembly 8. The power supply and control assembly 8 controls to light up the electronic cigarette.

The housing 1 can be made of a material or a combination of materials. The embodiments of suitable materials may include metals, alloy, etc. The shape of the housing 1 is not limited. In the illustrated embodiment (FIG. 13), the shape of the housing 1 substantially resembles a penholder. In other embodiments, the shape of the housing 1 could be a substantially cylinder or a cuboid.

An opening is defined on the top portion of the housing 1. The opening is configured to detachably connect to the cigarette holder 2, and the connection method is one of the threaded connection, clamped connection, or plugged connection. In the illustrated embodiment, the connection method is plugged connection. The inside upper end of the housing 1 is equipped with the liquid storing member 3, the atomizing head 4, the air inlet channel 5, and the air outlet channel 6. The inside lower end of the housing 1 is equipped with the power supply and control assembly 8.

The cigarette holder 2 can be made of any single material or a combination of materials. The materials can be the thermoplastic materials suitable for food or medical application, such as polypropylene, polyether-ether-ketone, and polyethylene. The materials also can be metal, alloy, and composite materials.

The cigarette holder 2 is a substantially hollow cylinder. In the first specific embodiment of the fifth embodiment, the cigarette holder 2 includes an upper segment (not shown in figures), and a lower segment fixed to the upper segment (not shown in figures). The upper segment is made of metal. The lower segment is made of silicone material. The upper segment enters the opening of the housing 1, and the upper segment abuts the internal wall of the housing 1.

In the illustrated embodiment (FIG. 13), the liquid storing member 3 is a substantially hollow cylinder, and in other embodiments, the shape of the liquid storing member 3 is not limited. The inside of the liquid storing member 3 is a liquid storing cavity 302. In the illustrated embodiment (FIG. 14), a sealing member 303 is positioned at the bottom center of the liquid storing cavity 302, or the whole bottom portion of the liquid storing cavity 302 can be a sealing member. The sealing member 303 is tightly coupled to the sidewall of the liquid storing member 3. Furthermore, the liquid storing member 3 is not transparent, to avoid deterioration of the stored liquid tobacco by light.

The power supply and control assembly 8 includes a battery 81 and a control plate 82. The control plate 82 is configured to control the atomizing head 4 and the sensor 7. A separation board 83 is positioned on the top of the power supply and control assembly 8. The separation board 83 is tightly coupled with the housing 1 to isolate the inside space of the housing 1. The battery 81 and the sensor are in the inside space of the housing 1.

The atomizing head 4 includes an atomizing head base 41, a head element 42, a liquid guiding element 44, an electrode contacting member 45, and a lancing member 43. An inner cavity 47 is positioned in the atomizing head base 41. The head element 42 and the liquid guiding element 44 are positioned in the inner cavity 47. The electrode contacting member 45 is detachably connected to the bottom of the atomizing head base 41. An end of the electrode contacting member 45 is electrically connected with the head element 42, and the other end of the electrode contacting member 45 is electrically connected with the control plate 82.

In the illustrated embodiment (FIG. 14), the liquid guiding element 44 may be made of fiber glass or natural fiber, such as cotton, fiber rope, etc. The heating element 42 is a thermal fuse. The heating element 42 is intertwined with the liquid guiding element 44. In other embodiments, the liquid guiding element 44 can be wrapped in the heating element 42. In order to absorb the liquid tobacco, a part of the liquid guiding element 44 extends into the liquid storing cavity 302.

The atomizing head base 41 defines a vent hole 46. In the illustrated embodiment (FIG. 14), the vent hole 46 is defined on the sidewall of the atomizing head base 41. The atomizing head base 41 defines an opening at the bottom. The opening of the base 41 communicates with the inner cavity 47 and the sensor 7 to let the air enter the sensor 7 and the atomizing head 4.

A supporting cylindrical member 304 is extended from the bottom of the liquid storing member 3. The supporting cylindrical member 304 is a hollow structure. A sealing member 303 is positioned on the top of the supporting cylindrical member 304. The bottom of the supporting cylindrical member 304 abuts the atomizing head base 41. The lancing member 43 inserts into the supporting cylindrical member 304, and the sealing member 303 is lanced by the lancing member 43, so that the liquid storing cavity 302 communicates with the atomizing head 4 and the inner cavity 47. Referring to FIG. 14, the external wall of the lancing member 43 abuts the internal wall of the supporting cylindrical member 304, to support the liquid storing member 3.

A supporting plate 9 is positioned at the bottom of the atomizing head 4. The atomizing head base 41 is arranged at the center gap of the supporting plate 9. The periphery of the supporting plate 9 is tightly coupled to the housing 1.

An air outlet channel 6 over the supporting plate 9 is formed by the space between the housing 1, the liquid storing member 3, and the atomizing head 4. The air outlet 6 communicates with the cigarette holder 2, the atomizing head 4, and the vent hole 46.

An air inlet 51 under the supporting plate 9 is defined on the housing 1. The air inlet 51 is located in the central position of the whole electronic cigarette. The space between the supporting plate 9 and the separation board 83 is an air inlet channel 5. The air inlet channel 5 communicates with the atomizing head base 41 and the air inlet 51. The sensor 7 is positioned in the air inlet channel 5 and adjacent to the air inlet 51. In the first specific embodiment of the fifth embodiment, the sensor 7 is plugged into the atomizing head base 41. The air flows into the air inlet 51, then passes through the air inlet channel 5 and the sensor 7. Finally, the air enters the inner cavity 47 of the atomizing head base 41.

The sealing member 303 is a substantially round tablet. The sealing member 303 can seal the liquid tobacco in the liquid storing cavity 302, so that the liquid tobacco will not leak. On the other hand, the sealing member 303 can be punctured easily by a sharp object, and the sealing member 303 may be made of aluminum foil, or non-woven fabric, etc. The liquid storing member 3 of the electronic cigarette can be replaced to extend the service life of the electronic cigarette.

The lancing member 43 is a substantially hollow needle. The liquid can flow in the inside of the lancing member 43. The lower end of the lancing member 43 is fixed to the atomizing head base 41, and the lancing member 43 communicates with the inner cavity 47. The lancing member 43 can puncture the sealing member 303 to let the liquid tobacco stored in the sealing member 303 flow into the atomizing head 4. The top of the lancing member 43 is an oblique incisor or a sharply raised portion. The lancing member 43 is made of metal or plastic.

The sensor 7 is an air flow sensor. In other embodiments, the sensor 7 can be an air pressure sensor. The air flow sensor 7 includes a feeler pin (not shown in figures) and an insulating cover with a contact (not shown in figures). The insulating cover (not shown in figures) is fixed to the housing 1 or the control plate 82. The contact (not shown in figures) is electrically connected with the control plate 82. When the feeler pin (not shown in figures) is connected with the contactor, the air flow is in the normal working condition. When the user inhales the electronic cigarette, the air flow sensor 7 forms a signal, and the signal is transmitted to the control plate 82. The control plate 82 controls the electronic cigarette to atomize the liquid tobacco.

Furthermore, in order to increase the stability and convenience of the air flow sensor 7, the air flow sensor 7 is positioned in the air flow sensor fixing seat (not shown in figures).

The air flow sensor fixing seat (not shown in figures) may be made of soft rubber material, such as acrylonitrile-butadiene-styrene (ABS), polycarbonate (PC), polyethylene (PE), polyformaldehyde (POM) and polypropylene (PP), polyvinyl chloride (PVC) and thermoplastic polyurethane elastomer (TPU), and rubber thermoplastic vulcanizate (TPV), etc.

A second specific embodiment of the fifth embodiment is as follows.

Referring to FIGS. 15-20, the methods of air flowing in and air flowing out are different from those of the first specific embodiment. The air inlet 51 is position on the housing 1 and adjacent to the top of the housing 1. A blocking portion 500 is positioned in the housing. Part of the edge of the blocking portion 500 is sealed with the internal wall of the housing 1. A groove 301 is defined on the sides of the lower portion of the blocking portion 500. The air inlet 51 is defined on the housing 1 to correspond to the groove 301. A first shell portion 600 is positioned in the housing 1. The first shell portion 600 is a substantially cylindrical structure. The upper end of the first shell portion 600 is connected with the lower end of the blocking portion 500. The bottom of the first shell portion 600 is spaced from the power supply and control assembly 8. An opening is defined at the bottom of the first shell portion 600. A stack outlet is formed between the blocking portion 500 and the housing 1.

The first shell portion includes a vertical wall 102, an upper periphery 101, and a lower periphery 107. The upper periphery 101 and the lower periphery 107 are positioned on the vertical wall 102. The lower periphery 107 is a ring, and tightly coupled to the internal wall of the housing 1.

Between the upper periphery 101 and the lower periphery 107, the space between the vertical wall 102 and the housing 1 forms an air outlet channel 6. The upper periphery 101 and the lower periphery 107 abut the internal wall of the housing 1 to support the housing 1. The vertical wall 102 includes two curved surfaces 1021. A vertical flat surface 1022 is configured to connect the two curved surfaces 1021.

An accommodation cavity 105 is positioned in the inside of the vertical wall 102 of the first shell portion 600. An air outlet 106 is defined on the wall of the accommodation cavity 105. The top of the vertical wall 102 is tightly coupled with the blocking portion 500. The air outlet 106 communicates with the air outlet channel 6. The liquid storing member 3 is positioned in the accommodation cavity above the air outlet 106. The atomizing head 4 is positioned under the air outlet 106.

A through groove 103 is defined in the vertical wall 102. In the second specific embodiment of the fifth embodiment, two through grooves 103 are defined on two sides of the vertical wall 102 to communicate with the grooves 301. The air inlet 5 is formed by the through grooves 103, the groove 301, and the space between the bottom of the first shell portion 600 and the power supply and control assembly 8.

Referring to FIG. 15, the sensor 7 is positioned in the groove 301. The sensor 7 is electrically connected with the control plate 82. When the user inhales, the external air enters the groove 301 by the side air inlets of the housing 1. When the external air passes through the sensor 7, an electrical signal produced by the sensor 7 is transmitted to control plate 82. The electronic cigarette is controlled to start working by the control plate 82, then the external air passes through the through groove 103 and the bottom opening of the first shell portion 106 to enter the atomizing head 4. The external air mixes with the smoke in the atomizing head 4. The air/smoke mixture passes the air outlet 106 and enters the air inlet 6. Finally, the air/smoke mixture flows out from the stack outlet 104 and the cigarette holder 2, and is inhaled by the user.

Referring to FIGS. 16, and 17, the sensor 7 can be positioned at the bottom of the atomizing head 4. The external air passes the air inlet 51, and enters the groove 301. Then, the external air passes through the through groove 103, the bottom opening of the first shell portion 600, and the sensor 7. Finally, the external air enters the atomizing head 4 from the top of the sensor 7.

In the second specific embodiment, the structure of the atomizing head 4, the liquid storing member 3, and the sensor 7 are same as in the first specific embodiment. The sealing member 303 is punctured by the lancing member 43, to let the inner cavity 47 of the atomizing head 4 communicate with the liquid storing cavity 302. The atomizing head 4 and the sensor 7 are electrically connected with the control plate 303. The smoke volume is greater by setting the blocking portion 500 and the first shell portion 600. Since the lower portion of the electronic cigarette is a sealing structure and the air inlet 51 is defined on the upper portion, this helps to prevent leakage.

A third specific embodiment of the fifth embodiment is as follows.

Referring to FIG. 22, the atomizing head 4 is positioned horizontally. The space for liquid storing member 3 is therefore increased.

Since the atomizing head 4 is positioned horizontally, the sealing member 303 is positioned vertically. The lancing member 43 punctures the sealing member 303, and is inserted into the liquid storing cavity horizontally.

A fourth specific embodiment of the fifth embodiment is as follows.

Referring to FIG. 21, the housing 1 is a detachable structure to facilitate the maintenance and replacement of the internal parts, especially of the sensor.

The housing 1 is divided into a first shell 110 and a second shell 120. The bottom of the first shell 110 defines external threads. The top portion of the second shell 120 defines internal threads. The first shell 110 and the second shell 120 are connected by the threads. A removable connecting structure 130 is positioned near the air inlet 51, to separate the housing 1. In an embodiment (FIG. 21), the first shell 110 is divided into a third shell 111 and a fourth shell 112. The third shell 111 and the fourth shell 112 are connected together by threaded connection, latched connection, plugged connection, or magnetic connection. In the illustrated embodiment, the connecting method is a latching structure 113. The third shell 111 can be separated from the fourth shell 112 by the latching structure 113 to change the liquid storing member 3 easily.

A fifth specific embodiment of the fifth embodiment is as follows.

Figure 24:
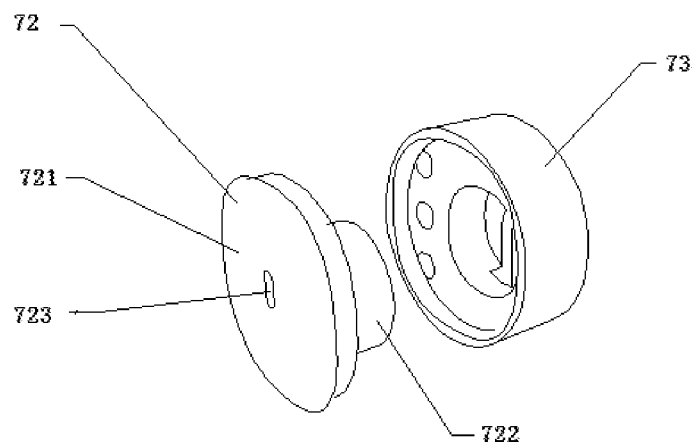
FIG. 24 is a schematic view of an air flow sensor module and a sealing base of the air flow sensor shown in FIG. 23.
Figure 25:
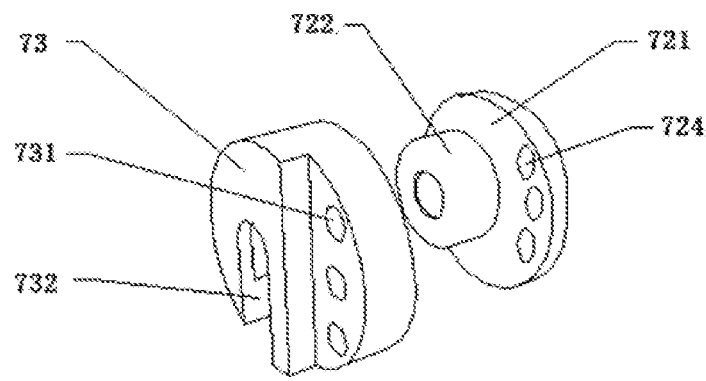
FIG. 25 is another schematic view of the air flow sensor module and the sealing base of the air flow sensor shown in FIG. 23.

Referring to FIGS. 23, 24, and 25, the position of the sensor 7 is different from the position in other embodiments. In the fifth specific embodiment, the sensor 7 is an air flow sensor.

The air flow sensor is located at the outside of the air inlet 51, and the air flow sensor is detachably connected with the housing 1. Therefore, the air flow sensor can be changed quickly.

An air flow sensor base 71 is positioned on the housing 1, and the air flow sensor base 71 is located at the outside of the air inlet 51. The air flow sensor base 71 includes a fixing member 711 and a PCB board 712. The fixing member 711 is positioned around the air inlet 51. The PCB board 712 is positioned in the fixing member. Pins 713 are positioned on the PCB board 712. The pins 713 are electrically connected with the control plate 82.

The fifth specific embodiment includes an air flow sensor module 72. The air flow sensor module 72 includes a PCBA board 721, and an air flow sensor body 722. A vent hole 723 is defined on the PCBA board 721 to correspond with the air flow sensor body 722. A contact is positioned on the PCBA board 721.

The air flow sensor further includes a sealing base 73. The sealing base could be made of silica gel. The sealing base 73 is covered by the PCBA board 721 and the air flow sensor body 722. A through hole 731 is defined on the sealing base to correspond with a contact 724. A vent groove 732 is defined on the sealing base 73 to correspond with the air flow sensor body 722. The pin 713 passes through the through hole 731 and abuts against the contact 724, so that the pin 713 is electrically connected with the contact 724. The through groove 732 communicates with the air inlet 51.

The air flow sensor further includes an air flow sensor rear cover 74. An air inlet is defined on the air flow sensor rear cover 74. The air inlet corresponds with the vent hole 723. The air flow sensor module 72 is positioned in the air flow sensor rear cover 74. The air flow sensor rear cover 74 is connected with the air flow sensor base 71 by threads, and the air flow sensor module 72 is fixed by connecting the air flow sensor rear cover 74 and the air flow sensor base 71 together. The pin 713 is electrically connected with the control plate 82.

In this way, the air flow sensor can be positioned at the top, middle, or bottom of the housing 1. When the sensor 7 is replaced, only the air flow sensor rear cover 74 needs to be unscrewed, then the whole air flow sensor module 72 can be changed. The connection method between the air flow sensor rear cover 74 and the air flow sensor base 71 can be replaced by latched connection, plugged connection, and magnetic connection.

Figure 26:
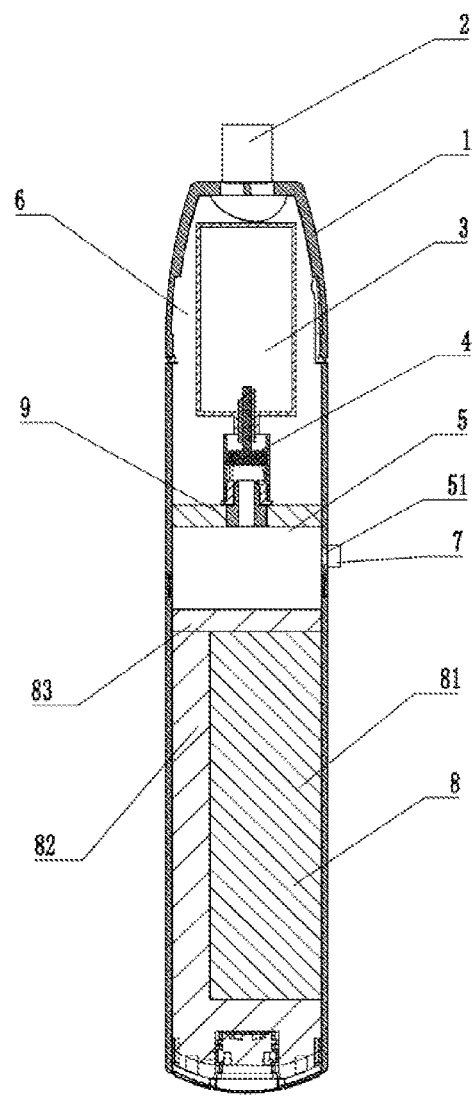
FIG. 26 is a schematic view of an electronic cigarette, in accordance with a fifth exemplary embodiment of the fifth embodiment.

Referring to FIG. 26, on the basis of the first specific embodiment, the sensor 7 is positioned at the outside of the air inlet 51, and the sensor 7 is detachably connected with the housing 1.

Figure 27:
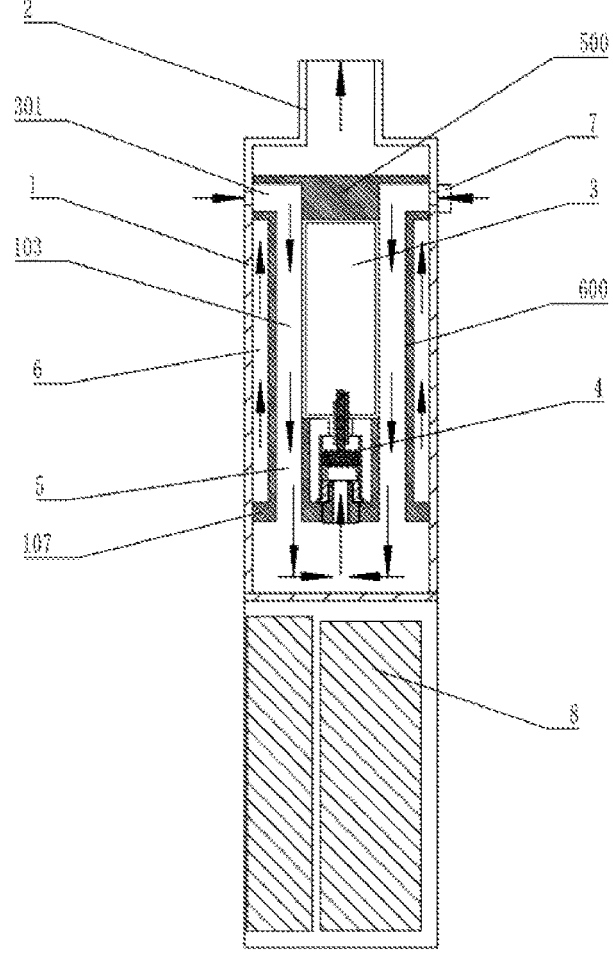
FIG. 27 is another schematic view of the electronic cigarette shown in FIG. 26.

Referring to FIG. 27, on the basis of the second specific embodiment, the sensor 7 is positioned at the outside of the air inlet 51, and the sensor 7 is detachably connected with the housing 1.

A sixth specific embodiment of the fifth embodiment is as follows.

On the basis of the first, or second, or third, or fourth, or fifth specific embodiments, the sixth embodiment includes a touch switch (not shown in figures), to prevent activating the electronic cigarette by mistake. The touch switch (not shown in figures) is positioned on the housing 1. In the sixth specific embodiment, the touch switch is an inductive sensor. The inductive sensor can be replaced by the resistive sensor, capacitive sensor, electromagnetic sensor, and eddy current sensor. The touch switch is electrically connected with the control plate 82. It is only when the touch switch is pressed while the user is inhaling that the electronic cigarette can be activated to heat the liquid tobacco. A USB port (not shown in figures) is positioned at the bottom of the electronic cigarette housing 1. The USB port (not shown in figures) is fixed to the control plate 82.

The embodiments shown and described above are only examples. Many details are often found in the art such as the other features of atomizers. Therefore, many such details are neither shown nor described. Even though numerous characteristics and advantages of the embodiments have been set forth in the foregoing description, together with details of the structure and function of the embodiments, the present disclosure is illustrative only, and changes may be made in details, including in the matters of shape, size, and arrangement of parts within the principles of the embodiments to the full extent indicated by the broad general meaning of the terms in which the appended claims are expressed.

What is claimed is:

1. An atomizer which comprises:
an outer tube,
a liquid storing member received in the outer tube, and
an atomizing head located at an end portion of the liquid storing member,
a liquid storing cavity formed in the liquid storing member, a liquid outlet communicating with the liquid storing cavity ands defined on the end portion of the liquid storing member;
an air outlet channel formed between the outer tube inner wall and the liquid storing member outer wall,
an atomizing cavity formed in the atomizing head, wherein the atomizing head comprises an atomizing head base, the atomizing cavity is formed in the atomizing head base, at least one liquid inlet groove communicating with the liquid outlet is defined on the sidewall of the atomizing head base along the axial direction of the atomizing head base, and at least one penetration hole communicating with the atomizing cavity is defined on a groove wall of the liquid inlet groove;
the atomizing cavity communicates with the liquid storing cavity and the air outlet channel, and
the liquid tobacco in the liquid storing cavity enters in the atomizing cavity to be atomized into mist, which mixes with air and then flows out through the air outlet channel.

2. The atomizer as claimed in claim 1 wherein:
the atomizer further comprises an atomizing tube sleeved on the atomizing head base, a heating element and a liquid guiding element,
the heating element and the liquid guiding element are received in the atomizing cavity and intertwined,
the liquid guiding element is attached to the penetration hole,
a first air outlet communicating with the atomizing cavity is defined on the atomizing head base,
a second air outlet aligned with the first air outlet is defined on the atomizing tube,
the second air outlet communicating with the air outlet channel and the first air outlet.

3. The atomizer as claimed in claim 1, wherein:
a liquid outlet communicating with the liquid storing cavity is defined on the end portion of the liquid storing member,
the atomizing head comprises an atomizing upper cover and an atomizing lower cover, and
the atomizing upper cover and the atomizing lower cover are connected with each other,
the atomizing upper cover is fixed to the end portion of the liquid storing member,
the atomizing upper cover is aligned with the liquid outlet, and
the atomizing cavity is formed by the space between the atomizing upper cover and the atomizing lower cover.

4. The atomizer as claimed in claim 3, wherein:
at least one air outlet communicating with the air outlet channel is defined on the atomizing upper cover, and
at least one second air inlet communicating with the atomizing cavity is defined on the atomizing upper cover.

5. The atomizer as claimed in claim 4, wherein:
the atomizing head further comprises a heating element and a liquid guiding element, the heating element and the liquid guiding element are received in the atomizing cavity and intertwined, the liquid guiding element is aligned with the liquid outlet.

6. The atomizer as claimed in claim 1, wherein:

a connecting portion is formed to be in communication with the liquid storing cavity by extending the end portion of the liquid storing member along the axial direction of the liquid storing member, the atomizing head comprises an atomizing head base, a liquid outlet communicating with the inner cavity of the connecting portion is defined on the sidewall of the connecting portion, a penetration hole aligned with the liquid outlet is defined on the sidewall of the atomizing head base, when the connecting portion is received in the atomizing head base, the liquid outlet is capable of being communicated with the penetration hole.

7. The atomizer as claimed in claim 6, wherein:

the atomizing head further comprises a heating element and a liquid guiding element each sleeved on the atomizing head base, the two sides of the liquid guiding element are respectively tightly attached to the heating element and the atomizing head base, the atomizing cavity is formed by the inner space of the heating element, a vent hole communicating with the atomizing cavity and the air outlet channel is defined on the heating element.

8. The atomizer as claimed in claim 1, wherein:

a liquid outlet communicating with the liquid storing cavity is defined on the end portion of the liquid storing member, the atomizing head comprises an atomizing head base, a heating element and a liquid guiding element, the heating element and the liquid guiding element are sleeved on the atomizing head base, the atomizing head base is arranged at the end portion of the liquid storing member and aligned with the liquid outlet, the end portion of the liquid storing member abuts the liquid guiding element.

9. An electronic cigarette comprising:

an atomizer, the atomizer comprises an outer tube, a liquid storing member received in the outer tube, and an atomizing head located at an end portion of the liquid storing member, a liquid storing cavity is formed in the liquid storing member, a liquid outlet communicating with the liquid storing cavity is defined on the end portion of the liquid storing member;

an air outlet channel is formed between the outer tube inner wall and the liquid storing member outer wall, an atomizing cavity is formed in the atomizing head, the atomizing head comprises an atomizing head base, the atomizing cavity is formed in the atomizing head base, at least one liquid inlet groove communicating with the liquid outlet is defined on the sidewall of the atomizing head base along the axial direction of the atomizing head base, and at least one penetration hole communicating with the atomizing cavity is defined on a groove wall of the liquid inlet groove; and the atomizing cavity communicates with the liquid storing cavity and the air outlet channel, the liquid tobacco in the liquid storing cavity enters in the atomizing cavity to be atomized into mist, which then flows out through the air outlet channel.

\* \* \* \* \*